United States Patent [19]

Hansen, Jr. et al.

[11] Patent Number: 5,364,850

[45] Date of Patent: Nov. 15, 1994

[54] SUBSTITUTED TYROSYL DIAMIDE COMPOUNDS

[75] Inventors: Donald W. Hansen, Jr., Skokie; Nizal S. Chandrakumar; Karen B. Peterson, both of Vernon Hills; Sofya Tsymbalov, Des Plaines; Robert K. Husa, Gurnee, all of Ill.

[73] Assignee: G. D. Searle & Co., Chicago, Ill.

[21] Appl. No.: 125,897

[22] Filed: Sep. 24, 1993

Related U.S. Application Data

[62] Division of Ser. No. 886,276, May 20, 1992, Pat. No. 5,272,175.

[51] Int. Cl.$^5$ .................... A61K 31/495; A61K 31/40; A61K 31/165; C07D 241/04
[52] U.S. Cl. ............................... 514/255; 514/423; 514/487; 514/539; 514/592; 514/595; 514/616; 544/387; 548/540; 560/25; 560/27; 560/34; 560/39; 564/42; 564/47; 564/56; 564/153; 564/157; 564/158
[58] Field of Search .................. 544/387; 548/540; 560/25, 27, 34, 39; 564/42, 47, 56, 153, 157, 158; 514/255, 423, 487, 539, 592, 595, 616

[56] References Cited

U.S. PATENT DOCUMENTS

| 4,599,325 | 7/1986 | Hansen et al. | 514/19 |
|---|---|---|---|
| 4,658,013 | 4/1987 | Morgan | 530/302 |
| 4,727,189 | 2/1988 | Hansen et al. | 564/155 |
| 4,760,180 | 7/1988 | Pitzele et al. | 564/157 |
| 4,797,470 | 1/1989 | Pitzele et al. | 530/331 |
| 5,169,833 | 12/1992 | Hansen et al. | 514/17 |
| 5,216,124 | 6/1993 | Hansen et al. | 530/317 |
| 5,292,726 | 3/1994 | Ashton et al. | 514/85 |

FOREIGN PATENT DOCUMENTS

| 0175323 | 3/1986 | European Pat. Off. . |
|---|---|---|
| 2923878 | 1/1981 | Germany . |
| 58-75724 | 11/1984 | Japan . |
| 59-157961 | 2/1986 | Japan . |

OTHER PUBLICATIONS

E. Schroder, et al. "Peptide Synthesis, V; Synthesis of Symmetrical . . . " *Liebigs Ann. Chem.*, 646, 101–118, 1961–USA.

R. J. Vavrek, et al. "Minimum Structure Opiods—Dipeptide . . . " *Peptides*, 2, 303–308, 1981–USA.

Y. Kiso, et al. "Synthesis and Activity of a Short Chain . . . " *Peptide Chemistry*, 65–70, 1981—Japan.

A. R. Jacobson, et al. "Minimum-Structure Enkephalin Analogues . . . " *J. Med. Chem.*, 32-1708-1717, 1989—USA.

A. Guglietta, et al. "Dimeric Dermorphin Peptides . . . " *Methan. and Find. Exp. Clin. Pharmacol.*, 11(11) 663–670, 1989—Spain.

*Primary Examiner*—Richard L. Raymond
*Attorney, Agent, or Firm*—Roberta L. Hastreiter; Roger A. Williams

[57] ABSTRACT

The present invention provides substituted tyrosyl diamide compounds of general Formula I:

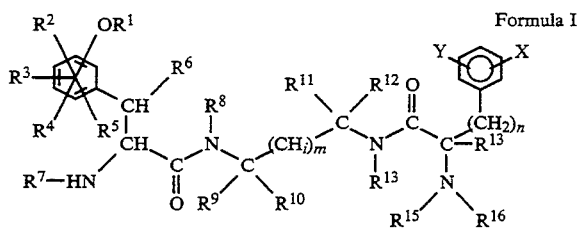

Formula I and the pharmaceutically-acceptable salts thereof, which are useful for inducing analgesia in animals, pharmaceutical compositions comprising a pharmaceutically-acceptable carrier and a compound of Formula I, and a method for inducing analgesia in an animal in need thereof comprising administering a therapeutically-effective amount of a compound of Formula I to the animal.

22 Claims, No Drawings

SUBSTITUTED TYROSYL DIAMIDE COMPOUNDS

This application is a divisional application of co-pending application Ser. No. 07/886,276, filed on May 20, 1992, now U.S. Pat. No. 5,272,175.

BACKGROUND OF THE INVENTION

(1). Field of the Invention

The present invention provides novel compounds having pharmaceutical activity which are useful as pharmaceutical agents and, more particularly, as analgesic agents for the treatment of pain in animals, pharmaceutical compositions containing one or more of these compounds, methods of use employing these compounds and methods of manufacturing these compounds.

More specifically, the present invention concerns: (1) substituted tyrosyl diamide compounds which, by apparently acting as neurotransmitters or neuromodulators in the central nervous pain-suppressant system, induce analgesia in animals; (2) pharmaceutical compositions containing one or more of these compounds in combination with a pharmaceutically-acceptable carrier; and (3) methods of treating pain employing these compounds.

Analgesic compounds are agents which alleviate pain without causing a loss of consciousness and, thus, which are useful for treating pain and, often, for reducing inflammation.

The major classes of analgesic compounds include analgesic-antipyretic compounds, which are compounds which alleviate pain and/or reduce fever, such as salicylates, and narcotic analgesics, or opiates, compounds which alleviate pain and/or induce sleep.

While salicylate and salicylate-like agents (non-steroidal antiinflammatory agents or NSAIDS) are efficacious in relieving pain, they often exhibit undesirable side effects, such as gastrointestinal irritation, including bleeding, as with aspirin, allergic response, as with aspirin, and/or liver toxicity with extended use, as with acetaminophen.

The compounds of the present invention are not salicylates, and represent another class of compounds which are useful as analgesic agents.

(2). Description of the Related Art

Opioids are a class of drugs which are, to varying degrees, opium-like or morphine-like in their properties. Although opioids are employed therapeutically primarily as analgesics, they have many other pharmacological effects as well, and they have some of the properties of certain naturally-occurring peptides.

By the year 1967, researchers working in the art had concluded that the complex interactions in the body between morphine agonists (morphine-like drugs) and mixed morphine agonist-antagonists could best be explained by postulating the existence of more than one type of cellular receptor for the opioids, and for related drugs.

Subsequent research in the area revealed that multiple categories of opioid receptors exist and, further, that there are at least three distinct families of naturally-occurring opioid peptides: (1) the endorphins; (2) the enkephalins; and (3) the dynorphins.

Although studies concerning the binding of opioid drugs and peptides to specific sites in the brain, and in other organs, have suggested the existence of, perhaps, as many as eight different types of opioid receptors in the body, there is reasonably firm evidence to support the conclusion that three major categories of opioid receptors, designated $\mu$, $\kappa$ and $\delta$, exist in the central nervous system. The classical opioid antagonist, naloxone, has been found to bind with high affinity to all three categories of opioid receptors.

The multiplicity of opioid receptor types in the central nervous system is now well established. Though much work has been directed at defining the structural elements that determine receptor specificity and efficacy, these factors are still, at best, poorly understood.

The rigid alkaloid opiates, typified by morphine, are generally believed to produce analgesia by interacting with the $\mu$ receptor.

It is now well established that the $\delta$ opioid receptor type mediates analgesia in the mouse, and that this site is generally associated with fewer gastrointestinal transit effects, and with less physical dependence, than the $\mu$ opioid receptor type.

In 1975, Hughes and Kosterlitz described the isolation of two naturally-occurring pentapeptides, "methionine enkephalin" (H$_2$N-Tyr-Gly-Gly-Phe-Met-OH) and "leucine enkephalin" (H$_2$N-Tyr-Gly-Gly-Phe-Leu-OH), from the brain. These pentapeptides occur in nerve endings of brain tissue, spinal cord and the gastrointestinal tract, bind to the same receptor sites as do the opiates, and exhibit some weak morphine-like actions, actions which were antagonized by naloxone.

That same year, Goldstein and his colleagues reported the presence of peptide-like substances in the pituitary gland which exhibited opioid activity.

The naturally-occurring pentapeptides isolated by Hughes and Kosterlitz appear to act as neurotransmitters or neuromodulators in the central nervous system, and bind stereospecifically to partially-purified brain opioid receptor sites. See, for example, Bradbury et al., *Nature*, 260, 793 (1976). These natural peptides are also highly active in bioassays for opioid activity, but exhibit only weak, fleeting analgesic activity when injected directly into the brain of the rat, and exhibit no activity when administered systemically in the rodent. See, for example, Belluzzi, et al., *Nature*, 260, 625 (1976).

In an attempt to overcome the lack of in vivo activity of the naturally-occurring pentapeptides isolated by Hughes and Kosterlitz, investigators working in the art have made numerous modifications to these enkephalins.

Among the modifications made to methionine enkephalin has been the synthesis of short-Chain, enkephalin-like peptides, among them dipeptide and tripeptide alkylamides, as described by Kiso et al., "Peptide Chemistry 1981," Protein Research Foundation, Osaka, Japan, 65–70 (1982).

Vavrek et al., Peptides, 2, 303 (1981), disclose analogs of the enkephalins, including the dipeptide, tyrosine-D-alanine-phenylpropylamide.

The large-scale use of synthetic enkephalins has been impractical due to various difficulties. One of the difficulties associated with natural enkephalins is that they are extremely unstable, and their half-lives in the blood are extremely short.

Attempts at solving these problems have focused upon altering the structure of the enkephalin molecule. Alterations in the enkephalin structure produce different pharmacological effects. To some degree, these effects are due to differential interactions with the various opioid receptors. However, it has been difficult to study the role of each receptor type, or to induce selectively the pharmacological and therapeutic effects associated with each receptor type, because the enkephalin analogs, to date, have had a high degree of selectivity for only the mu ($\mu$), rather than for the delta ($\delta$), opioid receptors.

For several years, the prototypic agonist for the $\delta$ opioid receptor has been the cyclic enkephalin analog [D-Pen$^2$, D-Pen$^5$]enkephalin. The recently-discovered deltorphins, heptapeptides of frog skin origin, are also highly selective and potent, in vitro, at this receptor. However, the relatively large size of these peptides suggest potential problems in crossing the blood brain barrier to elicit analgesia after systemic administration, a desirable property for a useful opioid analgesic. This has also hampered attempts to more fully define the functional role of $\delta$ receptors in the central nervous system.

Compounds within the present invention are tyrosyl diamide opioid agonists which have a substantial affinity for both the $\mu$ and the $\delta$ opioid receptors, and which produce analgesia following central and peripheral routes of administration in animals.

The compounds of the present invention are structurally distinct from that which has been described in the art.

Moreover, compounds of the present invention exhibit unexpected and surprisingly superior analgesic activity when compared to compounds of the prior art. These novel tyrosyl diamide compounds show improved potency and bioavailability as analgesic agents by central and peripheral routes of administration, such as by subcutaneous administration.

A. R. Jacobson et al., in "Minimum-Structure Enkephalin Analogues Incorporating L-Tyrosine, D (or L)-Phenylalanine, and a Diamine Spacer," *J Med Chem.*, 32, 1708–1717 (1989), disclose a series of compounds in which L-tyrosine was linked to N-acyl phenylalanine through a variety of diamine spacers. Tyrosyl diamide compounds within the present invention were found to be surprisingly and unexpectedly superior to the peptide compounds described by Jacobson et al., as will be discussed in more detail hereinbelow.

SUMMARY OF THE INVENTION

The present invention provides compounds having a structure of Formula I:

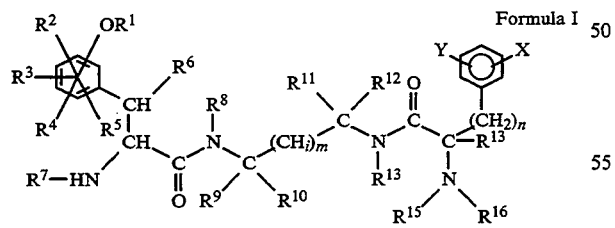

Formula I and the pharmaceutically-acceptable salts thereof, wherein:

$R^1$ is hydrogen, alkyl having from 1 to 4 carbon atoms or acetyl;

$R^2$, $R^3$, $R^4$, $R^5$, $R^6$, $R^{14}$ and $R^{15}$ may each be the same or different, and are each independently hydrogen or alkyl having from 1 to 4 carbon atoms;

$R^7$ is hydrogen or t-butyloxycarbonyl;

$R^8$ is hydrogen, alkyl having from 1 to 4 carbon atoms or may be taken together with $R^9$, $R^{10}$, —(-CH$_i$)$_m$—, $R^{11}$, $R^{12}$ and $R^{13}$ to form a single-ring, nonaromatic structure;

$R^9$ is hydrogen, alkyl having from 1 to 4 carbon atoms or may be taken together with $R^8$, $R^{10}$, —(-CH$_i$)$_m$—, $R^{11}$, $R^{12}$ and $R^{13}$ to form a single-ring, nonaromatic structure, or may be taken together with $R^{10}$, —(CH$_i$)$_m$—, $R^{11}$, $R^{12}$ and $R^{13}$ to form a single-ring, nonaromatic structure, or may be taken together with $R^{10}$, —(CH$_i$)$_m$—, $R^{11}$ and $R^{12}$ to form a single-ring, aromatic structure;

$R^{10}$ is hydrogen, alkyl having from 1 to 4 carbon atoms or may be taken together with $R^8$, $R^9$, —(-CH$_i$)$_m$—, $R^{11}$, $R^{12}$ and $R^{13}$ to form a single-ring, nonaromatic structure, or may be taken together with $R^9$, —(CH$_i$)$_m$—, $R^{11}$, $R^{12}$ and $R^{13}$ to form a single-ring, nonaromatic structure, or may be taken together with $R^9$, —(CH$_i$)$_m$—, $R^{11}$ and $R^{12}$ to form a single-ring, aromatic structure;

$R^{11}$ is hydrogen, alkyl having from 1 to 4 carbon atoms or may be taken together with $R^8$, $R^9$, $R^{10}$, —(CH$_i$)$_m$—, $R^{12}$ and $R^{13}$ to form a single-ring, nonaromatic structure, or may be taken together with $R^9$, $R^{10}$, —(CH$_i$)$_m$—, $R^{12}$ and $R^{13}$ to form a single-ring, nonaromatic structure, or may be taken together with $R^9$, $R^{10}$, —(CH$_i$)$_m$— and $R^{12}$ to form a single-ring, aromatic structure;

$R^{12}$ is hydrogen, alkyl having 1 to 4 carbon atoms or may be taken together with $R^8$, $R^9$, $R^{10}$, —(CH$_i$)$_m$—, $R^{11}$ and $R^{13}$ to form a single-ring, nonaromatic structure, or may be taken together with $R^9$, $R^{10}$, —(CH$_i$)$_m$—, $R^{11}$ and $R^{13}$ to form a single-ring, nonaromatic structure, or may be taken together with $R^9$, $R^{10}$, —(CH$_i$)$_m$— and $R^{11}$ to form a single-ring, aromatic structure;

$R^{13}$ is hydrogen, alkyl having 1 to 4 carbon atoms or may be taken together with $R^8$, $R^9$, $R^{10}$, —(CH$_i$)$_m$, $R^{11}$ and $R^{12}$ to form a single-ring, nonaromatic structure, or may be taken together with $R^9$, $R^{10}$, —(CH$_i$)$_m$—, $R^{11}$ and $R^{12}$ to form a single-ring, nonaromatic structure;

$R^{16}$ is hydrogen, acetyl,

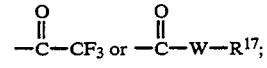

W is —CH$_2$—, oxygen or —NH—;

$R^{17}$ is alkyl, alkaryl, alkenyl, alkylcarboalkoxy or sulfonylaryl;

X is hydrogen, halogen or alkyl having from 1 to 4 carbon atoms;

Y is hydrogen or alkyl having from 1 to 4 carbon atoms;

i is an integer of from 0 to 2;

m is an integer of from 0 to 6; and n is an integer of from 0 to 6, with the proviso that $R^2$, $R^3$, $R^4$ and $R^5$ cannot each be hydrogen when:

(1) m is 0 or 1; and (2) n is 1; and (3) $R^{16}$ is acetyl; and (4) i is 2; and (5) $R^1$, $R^6$, $R^7$, $R^8$, $R^9$, $R^{10}$, $R^{11}$, $R^{12}$, $R^{13}$, $R^{14}$, $R^{15}$, X and Y are each hydrogen; or $R^9$ and $R^{10}$ are each methyl; or $R^{11}$ and $R^{12}$ are each methyl.

The present invention also provides pharmaceutical compositions which are pharmaceutically acceptable, and which comprise a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

DETAILED DESCRIPTION OF THE INVENTION

(1) Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The symbols " ▼ " and " ≡ " as used herein denote one of two possible stereoisomers.

The abbreviation "Ac" and the term "acetyl" as used herein mean the group

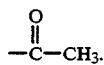

The abbreviation "acyl" as used herein means

The abbreviations "AcOH" and "HOAc" as used herein mean

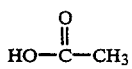

and acetic acid.

The term "alkyl" as used herein means a saturated hydrocarbon radical having from one to ten carbon atoms, within which includes from one to five carbon atoms, and further within which includes from one to three carbon atoms, which can be a straight or branched chain. Representative of such radicals are methyl, ethyl, n-propyl, isopropyl, n-butyl, sec-butyl, isobutyl, tert-butyl, 2-ethylhexyl and the like.

The term "alkylamino" as used herein means an alkyl radical, as defined above, having an amino group as defined below, attached thereto.

The term "alkylaminocarbonyl" as used herein means an alkylamino radical, as defined above, having a carbonyl group, as defined below, attached thereto.

The term "alkylcarbonyl" as used herein means an alkyl radical, as defined above, having a carbonyl group, as defined below, attached thereto.

The term "alkaryl" as used herein means an alkyl radical, as defined above, having one or more hydrogen atoms replaced by an aryl radical, as defined below.

The term "alkenyl" as used herein means a hydrocarbon radical having from one to ten carbon atoms, within which includes from one to five carbon atoms, and further within which includes from one to three carbon atoms, which can be a straight or branched chain, and which contains from one to two —CH=CH— groups.

The term "alkoxy" as used herein means an alkyl radical, as defined above, having an oxygen atom attached thereto. Representative alkoxy groups include methoxy, ethoxy, n-propoxy, tert-butoxy and the like.

The term "alkoxyaryl" as used herein means an alkoxy radical, as defined above, including an aryl radical, as defined below.

The term "alkoxycarbonyl" as used herein means an alkoxy radical, as defined above, including a carbonyl group, as defined below.

The term "alkylcarboalkoxy" as used herein means an alkylcarbonyl group, as defined above, which is attached to an alkoxy group, as defined above, through a

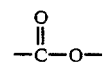

bond.

The term "alkynyl" as used herein means a hydrocarbon radical having from one to ten carbon atoms, within which includes from one to five carbon atoms, and further within which includes from one to three carbon atoms, which can be a straight or branched chain, and which contains from one to two —C≡C— groups.

The term "alkynylaryl" as used herein means an alkynyl group, as defined above, including an aryl group, as defined below.

The term "amino" as used herein means —NH₂.

The term "aminoacetyl" as used herein means

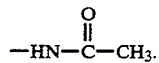

The term "aminocarbonyl" as used herein means

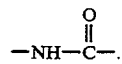

The term "analgesia" as used herein means the reduction, or absence, of sensibility to pain, designating particularly the relief of pain without loss of consciousness.

The term "animal" as used herein includes mammals and non-mammals, and further includes humans and non-human mammals.

The term "aryl" and the abbreviation "Ar" as used herein mean unsubstituted, mono- and/or di-substituted 5- and 6-membered single-ring aromatic radicals, for example, phenyl. In Formula I, and in the General Reaction Schemes contained herein, the term "aryl" and the abbreviation "Ar" in conjunction with the variables X and Y mean mono- or di-substituted 5- and 6-membered single-ring aromatic radicals.

The term "aralkyl" as used herein means an aryl radical, as defined above, having one or more hydrogen atoms replaced by an alkyl radical, as defined above, for example, N-methylpyrrolyl.

The abbreviation "Bzl" and the term "benzyl" as used herein means $C_6H_5CH_2$—.

The phrase "blood brain barrier" as used herein means a chemical barrier made up by the cell walls of the capillaries which are present in the brain tissues, through which drugs circulating in the blood must pass in order to have an effect in the central nervous system.

The abbreviation "Boc" as used herein means t-butyloxycarbonyl.

The abbreviation "Boc-D-Ala" as used herein means t-butyloxycarbonyl-D-alanine.

The phrase "Boc-DMT" as used herein means Boc-2,6-L-dimethyltyrosine.

The abbreviation "C" as used herein means the C or carboxy terminus of an amino acid or peptide or the element carbon, depending upon the context in which it is used, as is known by those of skill in the art.

The term "carbonyl" as used herein means

The term "carboxyl" as used herein means

The abbreviation "CH$_2$Cl$_2$" as used herein means methylene chloride.

The term "composition" as used herein means a product which results from the combining of more than one element or ingredient.

The term "dialkylaminocarbonyl" as used herein means

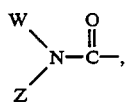

wherein W and Z are each independently alkyl, as defined above.

The term "dialkylamino" as used herein means

wherein W and Z are each independently alkyl, as defined above.

The abbreviation "DCC" as used herein means dicyclohexylcarbodiimide.

The abbreviation "DIEA" as used herein means diisopropylethylamine.

The abbreviation "DMF" as used herein means dimethylformamide.

The phrase "ED$_{50}$ value" as used herein means that dose of a compound or drug which produced a biological effect, such as producing analgesia, in 50% of the animals to which the compound or drug was administered.

The abbreviation "Et" as used herein means ethyl (—CH$_2$CH$_3$).

The abbreviation "Et$_2$O" as used herein means diethyl ether.

The term "Et$_3$N" as used herein means triethylamine.

The abbreviation "EtOAc" as used herein means ethyl acetate.

The abbreviation "EtOH" as used herein means ethanol (CH$_3$CH$_2$OH).

The term "halo" or "halogen" as used herein means chlorine (Cl), bromine (Br), fluorine (F) and/or iodine (I).

The term "heteroatom" as used herein means an atom of any element other than carbon or hydrogen.

The abbreviation "HOBT" as used herein means 1-hydroxybenzotriazole.

The term "hydroxy" as used herein means —OH.

The abbreviation "IBCF" as used herein means isobutylchloroformate.

The abbreviation "i.g." as used herein means that a compound or drug was administered intragastrically.

The abbreviation "Me" as used herein means methyl (—CH$_3$).

The abbreviation "MeOH" as used herein means methanol (CH$_3$OH).

The abbreviation "N" as used herein means the N or amino terminus of an amino acid or peptide and/or the element nitrogen, depending upon the context in which it is used, as is known by those of skill in the art.

The abbreviation "N-Ac-Phe" as used herein means N-acetyl-phenylalanine.

The acronym "NSAID" as used herein means nonsteroidal antiinflammatory drug, as discussed by J. G. Lombardino, Ed. *Nonsteroidal Antiinflammatory Drugs, Chemistry and Pharmacology of Drug Series*, Wiley, N.Y. (1985).

The term "nitro" as used herein means —NO$_2$.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The abbreviation "NMM" as used herein means N-methylmorpholine.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "pharmaceutically-acceptable salts" as used herein refers to non-toxic salts of the compounds of the present invention which are generally prepared by reacting the free base with a suitable organic or inorganic acid, or which are prepared by reacting the free acid with a suitable base. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, clavulanate and the like salts and alkali metal salts, such as sodium and potassium, and alkaline earth salts, such as calcium and magnesium.

The abbreviation "Ph" and the term "phenyl" as used herein means the group $C_6H_5$—, derived from benzene.

The abbreviation "p.o." as used herein means that a compound or drug was administered orally.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The phrase "N-protecting group" or "N-protected" as used herein means those groups intended to protect the N-terminus of an amino acid or peptide, to protect an amino group against undesirable reactions during synthetic procedures and includes, but is not limited to, sulfonyl, acyl, acetyl, pivaloyl, t-butyloxycarbonyl (Boc), benzyloxycarbonyl (Cbz), benzoyl and an L- or D-aminoacyl residue, which may itself be N-protected similarly.

The abbreviation "RaNi" as used herein means Raney nickel.

The abbreviation "s.c." as used herein means that a compound or drug was administered subcutaneously.

The term "sulfonylaryl" as used herein means

wherein Ar is as defined above.

The phrases "systemic administration" and "peripheral administration" as used herein mean the administration of a compound, drug or other material other than directly into the central nervous system, such that it enters the patient's system and, thus, is subject to metabolism and other like processes, for example, subcutaneous administration.

The abbreviation "TEAP" as used herein means triethylamine-phosphate buffer.

The abbreviation "TFA" as used herein means trifluoroacetic acid.

The phrase "therapeutically-effective amount" as used herein means that amount of a compound, material, or composition which is effective for eliminating or ameliorating pain in an animal, or for producing some other desired therapeutic effect, at a reasonable benefit/risk ratio applicable to any medical treatment.

The abbreviation "THF" as used herein means tetrahydrofuran.

The phrases "title compound," "title product," "title peptide" and "title material" as used herein mean that compound, product, peptide or material whose chemical name is given, and whose structure is shown, in the particular example, or subpart thereof, referred to. If no particular example, or subpart thereof, is referred to, it means that compound, product, peptide or material whose chemical name is given, and whose structure is shown, in the particular example, or subpart thereof, in which it appears.

The term "trifluoroacetyl" as used herein means $CF_3CH_2CO$—.

The phase "Z group" as used herein means benzyloxycarbonyl group.

The abbreviation "Z-Phe" as used herein means N-benzyloxycarbonyl-L-phenylalanine.

Amino acids appearing herein may be identified according to the following three-letter abbreviations.

| Amino Acid | Three-Letter Abbreviation |
|---|---|
| Alanine | Ala |
| Arginine | Arg |
| Asparagine | Asn |
| Aspartic Acid | Asp |
| Cysteine | Cys |
| Glutamine | Gln |
| Glutamic Acid | Glu |
| Histidine | His |
| Isoleucine | Ile |
| Leucine | Leu |
| Lysine | Lys |
| Methionine | Met |
| Penicillamine | Pen |
| Phenylalanine | Phe |
| Proline | Pro |
| Serine | Ser |
| Threonine | Thr |
| Tryptophan | Trp |
| Tyrosine | Tyr |
| Valine | Val |

The letters "L" and "D" appearing herein indicate whether a particular amino acid has the naturally-occurring configuration (L) or has the nonnaturally occurring configuration (D). Unless otherwise indicated, such as in the names or the structures for the various compounds appearing herein, the amino acids appearing herein are L-enantiomorphs, rather than D-enantiomorphs.

(2) Description of Invention

In one aspect, the present invention provides compounds comprising a structure of Formula I, as described above in the "Summary of Invention" section, which are pharmaceutically acceptable, and pharmaceutically-acceptable salts thereof.

The compounds of the present invention comprise a class of substituted tyrosyl diamide compounds which contain: (1) a tyrosine, or modified tyrosine, amino acid residue; (2) a diamine spacer unit located between a tyrosine, or modified tyrosine, amino acid residue and a phenylalanine, or modified phenylalanine, amino acid residue, which joins the two amino acid residues together through an amide linkage; and (3) a phenylalanine, or modified phenylalanine, amino acid residue.

Although the compounds of the present invention contain two amino acid residues, they are not dipeptide compounds, because they are structurally different from true dipeptide compounds. While a true dipeptide compound has the amino-terminus of the second amino acid residue in the sequence joined by a peptide linkage to the carboxy-terminus of the first amino acid residue in the sequence, the tyrosyl diamide compounds of the present invention have the carboxy-terminus of the second amino acid residue in the sequence joined to a diamine spacer arm, with the diamine spacer arm being joined to the carboxy-terminus of the first amino acid residue in the sequence. Thus, as is illustrated directly below, the second amino acid residue in the sequence is inverted, so that the left end of the residue is the carboxy terminus of the amino acid, and the right end of the residue is the amino-terminus of the amino acid.

Tyrosyl Diamide Compounds of the Invention

| Amino Acid No. 1 | | Amino Acid No. 2 |
|---|---|---|
| [Amino   [Carboxy | – Diamine – | [Carboxy   [Amino |
| Terminus] Terminus] | Spacer Arm | Terminus] Terminus] |

The diamine spacer arm which links the two amino acid residues together contains two —NH groups, which may be connected directly together to form an —NH—NH— group, or which may include straight- or branched-chain alkyl radicals between the two nitrogen atoms, preferably having from 1 to 4 carbon atoms. For example, the compound described in Example 47 has the following diamine spacer arm:

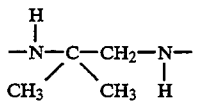

Preferably, the diamine spacer arm contains the two nitrogen atoms separated by a —CH$_2$—CH$_2$—group.

Preferred compounds of the present invention are those in which the R$^9$ and R$^{10}$ positions thereof, as shown in Formula I, are each methyl. The most preferred compound of the present invention is the compound shown and described in Example 47.

Specific compounds contemplated as falling within the scope of the invention include, but are not limited to, the compounds discussed in the examples presented below, as well as their pharmaceutically-acceptable salts.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of this invention may exist in geometric or stereoisomeric forms. The present invention contemplates all such compounds, including cis- and transgeometric isomers, R- and S-enantiomers, diastereomers, d-isomers, l-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Certain compounds of the present invention may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, S. M. Berge et al., "Pharmaceutical Salts," *J. Pharm. Sci.*, 66:1–19 (1977).)

In other cases, the compounds of the invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S. M. Berge et al.. "Pharmaceutical Salts," supra.)

In another aspect, the present invention provides pharmaceutically-acceptable compositions which comprise a therapeutically-effective amount of one or more of the compounds of Formula I, as described hereinabove, formulated together with one or more pharmaceutically-acceptable carriers. As described in detail below, the pharmaceutical compositions of the present invention may be specially formulated for oral administration in solid or liquid form, for parenteral injection, or for rectal or vaginal administration.

In yet a further aspect, the present invention provides a method for eliminating or ameliorating pain in an animal comprising administering a therapeutically-effective amount of a compound of Formula I, as described hereinabove, to the animal.

(3) Utility

By virtue of their analgesic activity, the compounds of the present invention, and the pharmaceutical compositions comprising one or more of these compounds, are useful as analgesic agents for the elimination or amelioration of pain in animals.

(4) Methods of Preparation

In general, the compounds of the present invention may be prepared by the methods illustrated in the following general reaction schemes, or by modifications thereof, using readily available starting materials, reagents and conventional synthetic procedures. In these reactions, it is also possible to make use of variants which are in themselves known, but are not mentioned here.

Unless otherwise specified, the various substituents of the compounds shown in the general reaction schemes are defined in the same manner as they are defined above in Formula I in the "Summary of Invention" section.

If a particular enantiomer of a compound of the present invention is desired, it may be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In General Reaction Scheme No. 1, a substituted or unsubstituted diamine is reacted with one equivalent of para-toluenesulfonic acid and one equivalent of benzyloxy chloroformate. The resulting mono N-benzyloxycarbonyl protected diamine is treated with an 'activated' N-Boc protected α-amino acid. The two methods of amino acid activation used are: (1) mixed anhydride coupling, which involves treatment of the acid with one equivalent each of N-methylmorpholine and isobutylchloroformate; and (2) carbodiimide coupling, which involves treatment of the acid with the appropriate amine, dicyclohexylcarbodiimide and hydroxybenzotriazole. Both of these methods of amino acid activation are known by those of skill in the art. The product of this reaction is either treated with acid to remove the Boc protecting group or treated with hydrogen in the presence of palladium on carbon to give Compounds A. Compounds A are also obtained in one step by the coupling of the N-Boc protected α-amino acid with an unprotected diamine in the presence of one equivalent of para-toluenesulfonic acid. Compounds A are coupled to an 'activated' N-benzyloxycarbonyl protected α-amino acid to give Compounds B. Compounds B are either treated with acid to remove the Boc protecting group or treated with hydrogen in the presence of palladium on carbon to give Compounds C. The amino group in Compounds A and C are suitably functionalized as outlined in this scheme, and as illustrated in the examples, to give a variety of compounds. Thus, for example, treatment of the amines with isocyanates gave urea-type compounds, and treatment of the amines with activated acids gave amide-type compounds. The resulting products of these functionalization reactions are treated with acid to provide the salts of the diamides indicated in Formula I.

General Reaction Scheme No. 2 outlines alternative and complementary procedures used for synthesizing compounds of this invention. Thus, in this scheme, a diamine is coupled to two α-amino acids in succession using a carbodiimide coupling procedure or mixed anhydride coupling procedure to afford the Compounds D. When $R^{16}$=acetyl, Compounds D are treated with acid to remove the Boc protecting group; when, in $R^{16}$, W=oxygen and $R^{17}$=benzyl, Compounds D are identical to Compounds B in General Reaction Scheme No. 1, and are treated in a similar fashion.

GENERAL REACTION SCHEME NO. 1

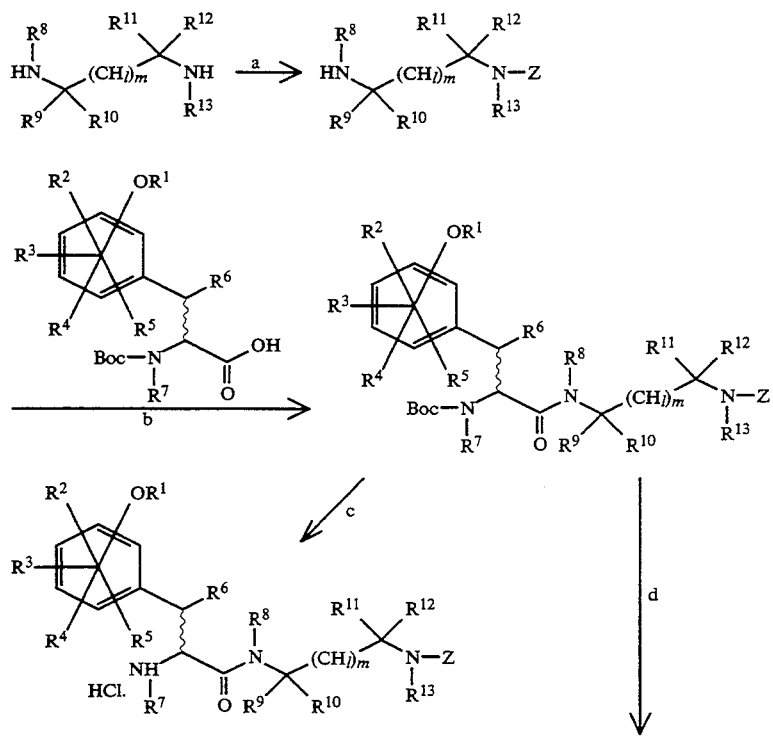

-continued
GENERAL REACTION SCHEME NO. 1
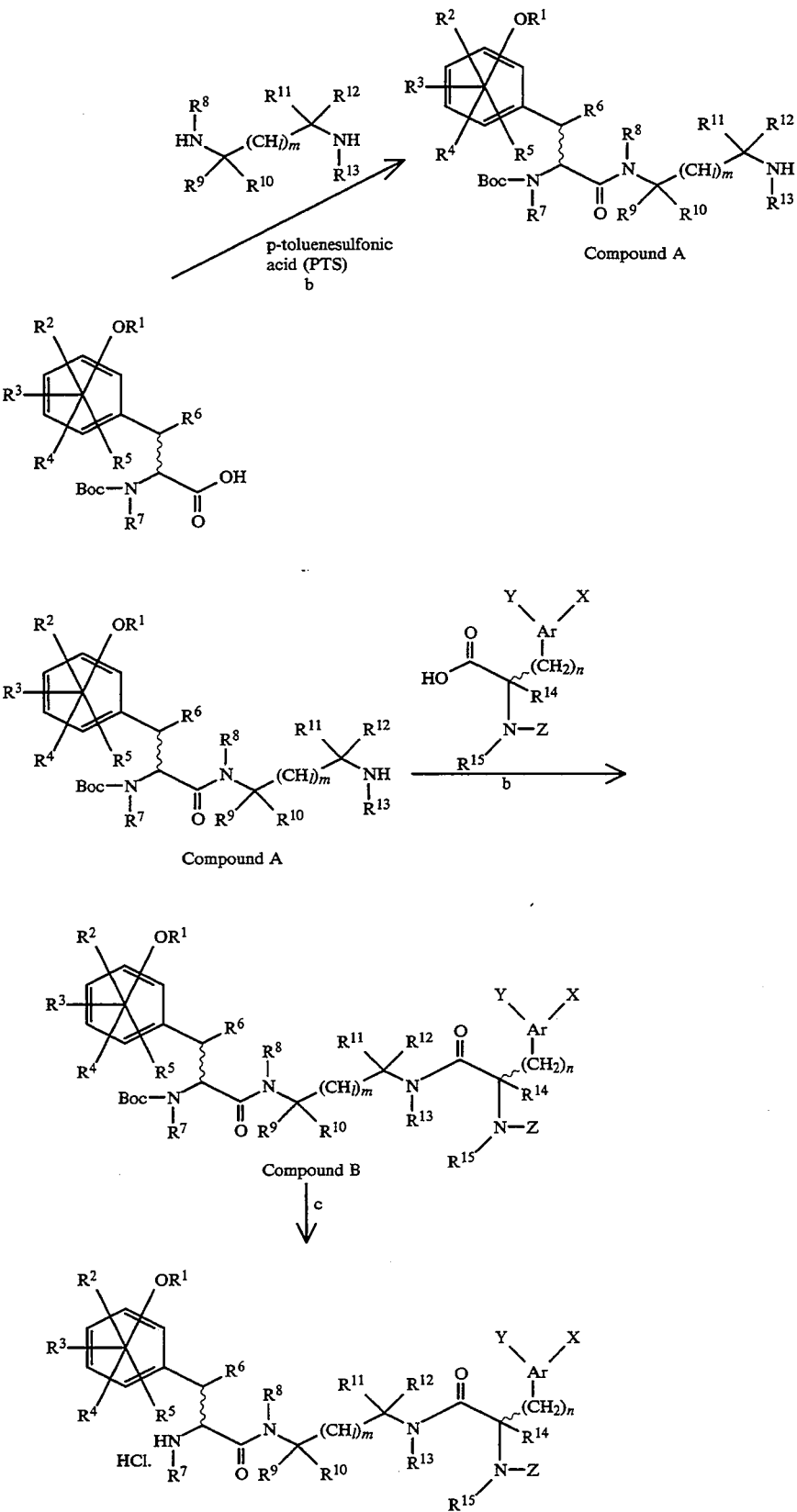

-continued
GENERAL REACTION SCHEME NO. 1

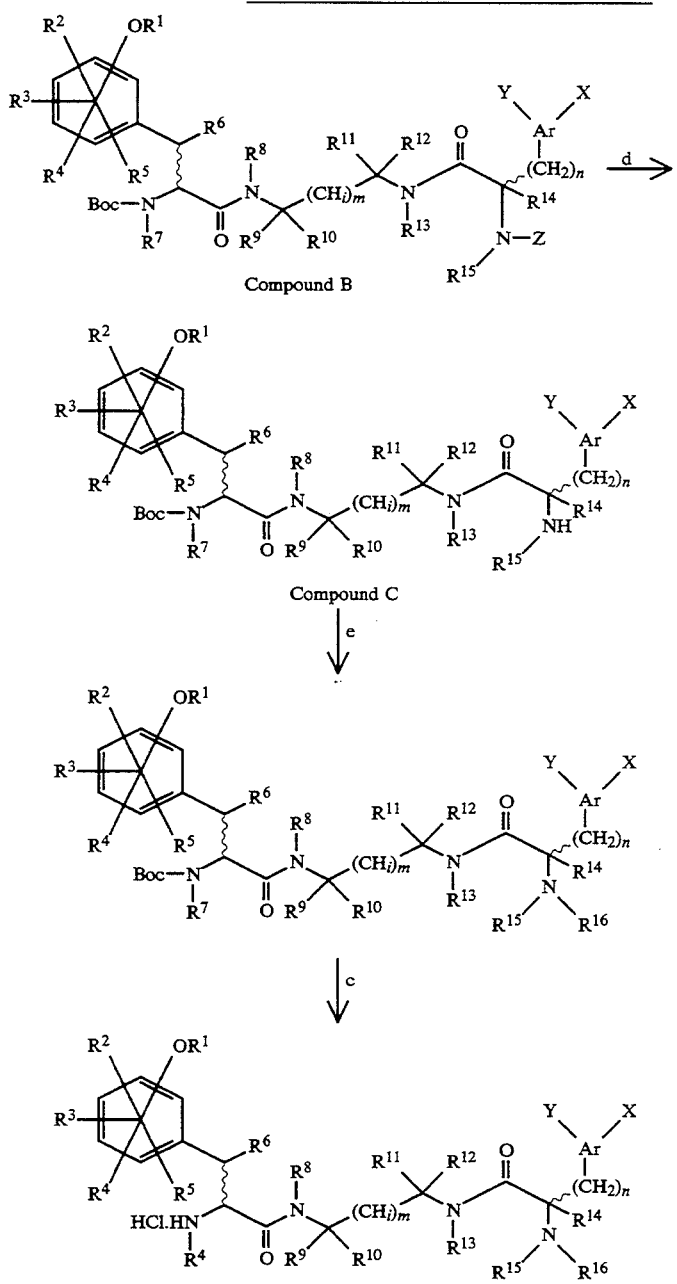

The following letters correspond to the same letters employed in General Reaction Scheme No. 1:
a) One equivalent each of para-toluenesulfonic acid and benzyloxychloroformate (Z=benzyloxycarbonyl).
b) Isobutyl chloroformate, N-methylmorpholine (mixed anhydride coupling) or dicyclohexyl carbodiimide and hydroxybenzotriazole (carbodiimide coupling).
c) HCl in dioxane-acetic acid or HCl in dioxane-$CH_2Cl_2$.
d) Hydrogen/Palladium on Carbon.
e) Introduce $R^{16}$ group:
For $R^{16}$=trifluoroacetyl:
  (1) trifluoracetic anhydride, dimethylaminopyridine, N-methylmorpholine in $CH_2Cl_2$; and
  (2) 15% $K_2CO_3$ in MeOH.
For $R^{16}$=acetyl:
  (1) acetic anhydride, dimethylaminopyridine, N-methylmorpholine in $CH_2Cl_2$; and
  (2) 15% $K_2CO_3$ in MeOH.
For $R^{16}$, where W=$CH_2$ and $R^{17}$=alkyl or alkaryl: treat Compounds A with alkyl or alkaryl carboxylic acids under mixed anhydride coupling conditions (see "b" above).
For $R^{16}$, where W=NH and $R^{17}$=alkyl, alkenyl or alkylcarboalkoxy: treat Compounds A with alkyl, alkenyl, or carboxyalkyl alkyl isocyanate.
For $R^{16}$, where W=NH and $R^{17}$=sulfonylaryl: treat Compounds A with arylsulfonylisocyanate.

GENERAL REACTION SCHEME NO. 2

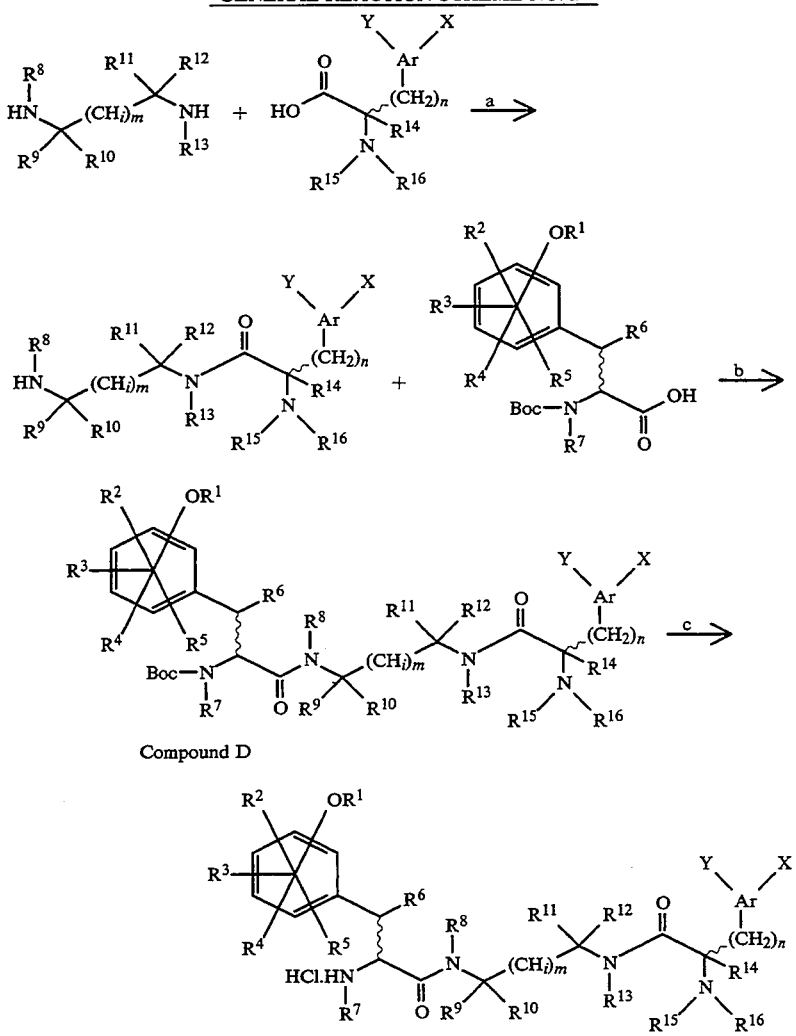

The following letters correspond to the same letters employed in General Reaction Scheme No. 2:

a) Isobutylchloroformate, N-methylmorpholine (mixed anhydride coupling) or dicyclohexylcarbodiimide and hydroxybenzotriazole (carbodiimide coupling) in the presence of one equivalent of para-toluenesulfonic acid.

b) Identical coupling conditions are used as in "a" above, except that para-toluenesulfonic acid was not used. The Compounds D obtained are identical to the Compounds B of General Reaction Scheme No. 1 where, in $R^{16}$, W=oxygen and $R^{17}$=benzyl. Compounds B here and in General Reaction Scheme No. 1 are used in an identical fashion to afford the various target structures represented by Compounds C.

When $R^{16}$=acetyl, Compounds D were treated with HCl in dioxane to remove the Boc protecting group. In $R^{16}$, where W=oxygen and $R^{17}$=benzyl, Compounds D are identical to Compounds B of General Reaction Scheme No. 1 and are treated in like fashion.

The conditions for carrying out the individual steps in each of the general reaction schemes presented above are conventional, well-known, and capable of wide variation.

Other methods known in the art can also be used to synthesize the compounds of the present invention.

(5) Dosage and Mode of Administration

The compounds of the present invention, and the pharmaceutical compositions comprising one or more of these compounds in combination with a pharmaceutically-acceptable carrier, are useful for treating pain in animals. A physician or veterinarian of ordinary skill in the art can readily determine whether or not a patient is in pain.

The pharmaceutical compositions of the present invention, which will typically comprise one or more of the compounds of Formula I, as described in the "Summary of Invention" section, as an active ingredient in a mixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices. The pharmaceutical compositions of the present invention may be specially formulated for oral administration in solid or liquid form, for parenteral injection, and/or for rectal or vaginal administration. These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are oral and subcutaneous, the most preferred mode of administration is subcutaneous.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day. If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, releasing agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediaminetetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, with one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient (compound of Formula I), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable mediums just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

While the various aspects of the present invention are described herein with some particularity, those of skill in the art will recognize numerous modifications and variations which remain within the spirit of the invention. These modifications and variations are within the scope of the invention as described and claimed herein.

(6) EXAMPLES

The following non-limiting examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention, and the pharmaceutical compositions comprising such compounds.

All patents and publications referred to in the examples, and throughout the specification, are hereby incorporated herein by reference, without admission that such is prior art.

In the examples, all parts are by weight, and all temperatures are degrees Celsius, unless otherwise noted. Unless otherwise noted, Infrared (IR) and Nuclear Magnetic Resonance (NMR) spectra were consistent with the assigned structure.

Unless otherwise indicated, all of the equipment employed in the examples is commercially available.

All starting materials used in the examples are commercially available, and were obtained from Aldrich Chemical Co. (Milwaukee, Wis.), TCI American Tokyo (Portland, Oreg.), Advanced Chemtech (Louisville, Ky.), Fluka Chemical Corp. (Ronkonkoma, N.Y.), Bachem Bioscience Inc. (Philadelphia, Pa.), Chemical Dynamics Corp. (South Plainfield, N.J.), Sigma Chemical Co. (St. Louis, Mo.) and/or Peptides International (Louisville, Ky.).

While Examples 1–59 describe specific methods for synthesis of compounds within the present invention, Examples 60–62 describe four different assays which were conducted with compounds of the present invention.

Examples 60 (Writhing Assay) and 61 (Tail Flick and Hot Plate Assays) describe experiments which were conducted to compare the analgesic activity of tyrosyl diamide compounds described herein with a compound described by A. R. Jacobson et al., supra., designated the "Jacobson Compound," in different analgesic assays, as described in detail hereinbelow.

The structure of the Jacobson Compound is shown below.

Jacobson Compound

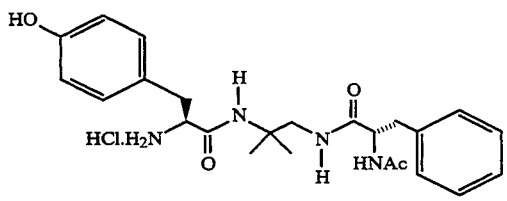

The tyrosyl diamide compound which is shown and described in Example 47 was tested in each of the following three analgesic assays, as described in Examples 60 and 61 hereinbelow: (1) the Writhing Assay; (2) the Tail Flick Assay; and (3) the Hot Plate Assay. These assays were performed in the manner described in Examples 60 and 61 hereinbelow. This compound, as well as the Jacobson Compound, was administered to the mice employed in these assays subcutaneously or orally, as indicated in the tables of data presented in Examples 60 and 61 hereinbelow.

Example 62 describes the evaluation of compounds within the present invention, as well as the Jacobson Compound, in an opioid radioligand binding assay, which measures the affinity of opioids for specific opioid receptors in rat forebrain, by their ability to displace the binding of radiolabeled ligands specifically bound to $\mu$ and/or $\delta$ opioid receptors isolated from rat brain.

Example 1

Phenylmethyl(2-amino-2-methylpropyl) carbamate

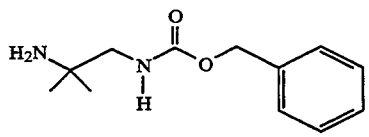

A solution of benzyloxychloroformate (3.9 g) in toluene (15 mL) was added dropwise to a stirred solution of 1,2-diamino-2-methylpropane (5 g) in toluene (90 mL) at 0° C. for 20 minutes. After 40 hours, the reaction mixture was filtered. The filtrate was concentrated in vacuo. The residue was redissolved in toluene and stripped of all solvent several times. The residue was dried in vacuo to give the title compound as a white solid (4.3 g), which was used in Example 2 without further purification.

Example 2

Phenylmethyl[2-[[2S-[[(1,1-dimethylethoxy)carbonyl]amino]-3-(4-hydroxy-2,6-dimethylphenyl)-1-oxopropyl]amino]-2-methylpropyl]carbamate

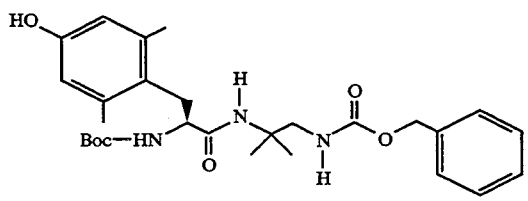

To a stirred solution of Boc-2,6-L-dimethyltyrosine (Boc-DMT, 13.9 g) in methylene chloride ($CH_2Cl_2$, 600 mL) at −78° C. was added N-methylmorpholine (NMM, 4.9 mL) followed by isobutylchloroformate (IBCF, 6.1 mL). The mixture was allowed to warm to 0° C. over 25 minutes and was then recooled to −78° C. To this was added the title compound of Example 1 (10 g), and stirring was continued for 48 hours. The mixture was concentrated in vacuo. The residue was dissolved in ethyl acetate (EtOAc), washed with 0.5 N $KHSO_4$, dried over $Na_2SO_4$, and concentrated in vacuo. The residue was purified by chromatography over silica gel using 5% ethanol in 8:11 $CH_2Cl_2$/n-hexane as eluant to give 8.9 g of the title compound as a white solid.

Example 3

Phenylmethyl]2-[[2S-amino-3-(4-hydroxy-2,6-dimethylphenyl)-1-oxopropyl]amino]2-methylpropyl]carbamate, monohydrochloride

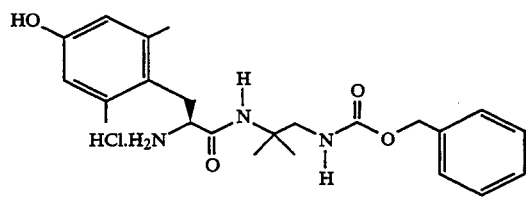

The title compound of Example 2 (0.4 g) was dissolved in 10 mL of acetic acid (HOAc) and 1.2 mL of 7N hydrogen chloride (7N HCl) in dioxane. The resulting solution was allowed to stir at room temperature for 30 minutes. The volatiles were removed in vacuo. The residue was triturated with diethyl ether ($Et_2O$), filtered and dried in vacuo to give the title compound as a white solid.

Calculated for $C_{23}H_{32}N_3O_4 + 0.4\ H_2O + HCl$ (MW=457.18): C, 60.43; H, 7.23; N, 9.19; Cl, 7.75. Found: C, 60.45; H, 7.22; N, 8.86; Cl, 7.67. $[\alpha]_D = +69.5°$, MeOH.

Example 4

Compound A 1,1-Dimethylethyl[1S-[[(2-amino-1,1-dimethylethyl)amino]carbonyl]-2-(4-hydroxy-2,6-dimethylphenylphenyl)ethyl]carbamate

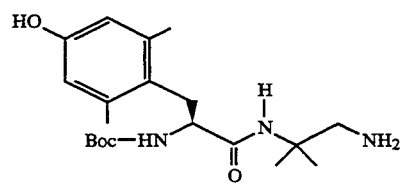

Compound B 1,1-Dimethylethyl[2-[(2-amino-2-methylpropyl)amino]-1S-[(4-hydroxy-2,6-dimethylphenyl)methyl]-2-oxoethyl]carbamate

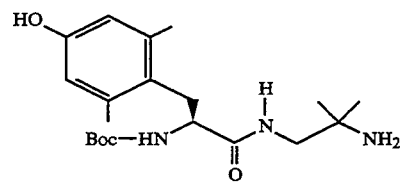

The title compound of Example 2 (6.07 g) was subjected to hydrogenation by a standard Parr apparatus in 100 mL of methanol (MeOH) with 4% Pd on carbon under 5 psi hydrogen for 16 hours. The mixture was filtered to remove the catalyst. The filtrate was concentrated to dryness to leave 4.3 g of a mixture of the title compounds as white solids.

Example 5

1,1-Dimethylethyl[1S-[[[2-[[2S-(acetylamino)-3-(4-fluorophenyl)-1-oxopropyl]amino]-1,1-dimethylethyl]amino]carbonyl]-2-(4-hydroxy-2,6-dimethylphenyl)ethyl]carbamate

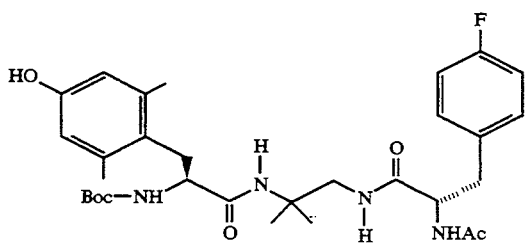

The product mixture of the title compounds of Example 4 was coupled to N-acetyl-L-p-fluoro-phenylalanine using the mixed anhydride coupling method as described in Example 2 above. The crude product was chromatographed over silica gel to give only the title compound as a white solid.

Example 6

αS-(Acetylamino)-N-[2-[[2S-amino-3-(4-hydroxy-2,6-dimethylphenyl)-1-oxopropyl]amino]-2-methylpropyl]-4-fluorobenzenepropanamide, monohydrochloride

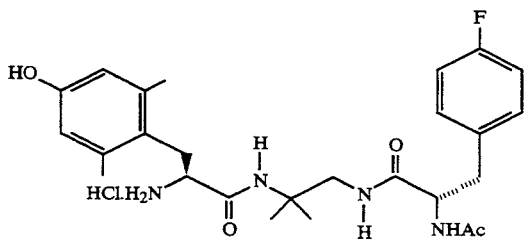

The title compound of Example 5 was treated with HCl by the procedure of Example 3 to give the title compound as a white solid salt.

$H^1$NMR (CD$_3$OD) δ: 0.94 (s, 3H), 1.15 (s, 3H), 2.28 (s, 6H). Calculated for: $C_{26}H_{35}N_4O_4F_1 + 1\ H_2O - 1\ HCl$ (MW=541.07): C, 57.72; H, 7.08; N, 10.35; Cl, 6.55. Found: C, 57.90; H, 6.98; N, 9.93; Cl, 6.57. [α]$_D$= +77.6°, MeOH.

Example 7

Phenylmethyl[1S-[[[2-[[2S-[[(1,1-dimethylethoxy)carbonyl]amino]-3-(4-hydroxy-2,6-dimethylphenyl)-1-oxopropyl]amino]-2-methylpropyl]amino]carbonyl]-2-(4-fluorophenyl)ethyl]carbamate

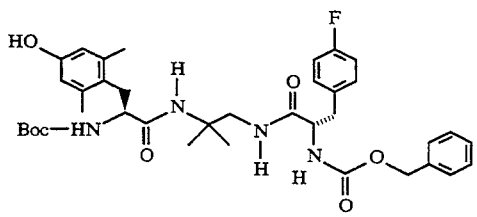

The product mixture of the title compounds of Example 4 was coupled to N-benzyloxycarbonyl-L-para-fluoro-phenylalanine using the mixed anhydride coupling method as described in Example 2 above. The crude product was chromatographed over silica gel to give only the title compound as a white solid.

Example 8

Phenylmethyl[1S-[[[2-[[2S-amino-3-(4-hydroxy-2,6-dimethylphenyl-1-oxopropyl]amino]-methylpropyl]amino]carbonyl]-2-(4-fluorophenyl)ethyl]carbamate, monohydrochloride

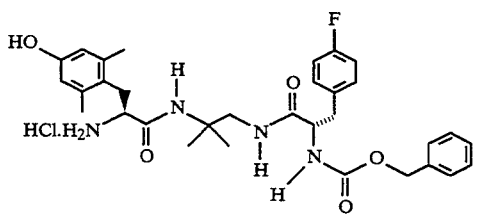

The title compound of Example 7 was treated with HCl by the procedure of Example 3 to give the title compound as a white solid.

$H^1$NMR (CD$_3$OD) δ: 0.9 (s, 3H), 1.2 (s, 3H), 2.3 (s, 6H). Calculated for: $C_{32}H_{39}N_4O_5F_1 + 0.5\ H_2O + 1\ HCl$ (MW=624.16): C, 61.58; H, 6.62; N, 8.98; Cl, 5.68. Found: C, 61.49; H, 6.53; N, 8.77; Cl, 5.76. [α]$_D$= +15.7°, MeOH.

Example 9

Phenylmethyl[1S-[[[2-[[2S-[[(1,1-dimethylethoxy)carbonyl]amino]-3-(4-hydroxy-2,6-dimethylphenyl)-1-oxopropyl]amino]-2-methylpropyl]amino]carbonyl]-2-phenylethyl]carbamate

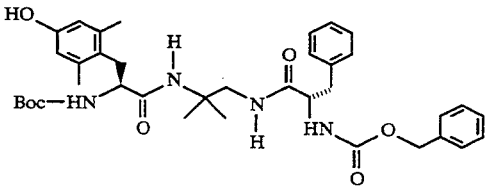

1,2-Diamino-2-methylpropane was coupled to benzyloxycarbonyl Z-phenylalanine and Boc-DMT in succession using the protocol of A. R. Jacobson et al., supra., which is incorporated herein by reference, to give the title compound as a white solid.

Briefly, to 15 mL of DMF was added 1.43 g of z-phenylalanine-OH, 426 mg of 1,2-diamino-2-methylpropane, 920 mg of para-toluenesulfonic acid mono hydrate and 652 mg of 1-hydroxybenzotriazole. After allowing the mixture to mix for 5 minutes, 1.1 g of 1,3-dicyclohexyl-carbodiimide was added and the reaction was mixed overnight at room temperature. The solvent was removed in vacuo and 50 mL of CHCl$_3$ was added. The mixture was then filtered and extracted with two 20-mL portions of half-saturated aqueous Na$_2$CO$_3$. The organic layer was concentrated in vacuo giving 625 mg of a white solid. To a 20-mL CH$_2$Cl$_2$ solution of this solid was added 0,494 g of Boc-DMT and 0.220 g of 1-hydroxybenzotriazole hydrate. After stirring for 5 minutes, 0.33 g of 1,3-dicyclohexyl-carbodiimide was added and the reaction mixture was allowed to warm to room temperature overnight with mixing. After filtration, the mother liquor was washed with two 20-mL portions of half-saturated Na$_2$CO$_3$ and evaporated to dryness in vacuo to give 1 g of the title compound as a white solid.

Example 10

Phenylmethyl[1S-[[[2-[[2S-amino-3-(4-hydroxy-2,6-dimethylphenyl)-1-oxopropyl]amino]-2-methylpropyl]amino]carbonyl]-2-phenylethyl]carbamate, monohydrochloride

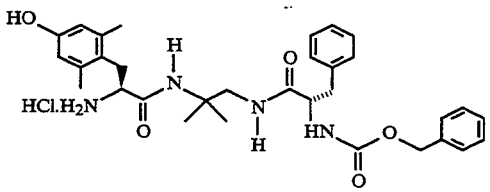

The title compound of Example 9 was treated with HCl by the procedure of Example 3 to give the title compound as a white solid.

H$^1$NMR (CD$_3$OD) δ: 0.9 (s, 3H), 1.2 (s, 3H), 2.3 (s, 6H), 6.6 (s, 2H). Calculated for C$_{32}$H$_{40}$N$_4$O$_5$+HCl+0.5 H$_2$O (MW=606.17): C, 63.41; H, 6.98; N, 9.24; Cl, 5.85. Found: C, 63.30; H, 7.04; N, 9.08; Cl, 6.33. [α]$_D$= +69.4°, MeOH.

Example 11

1,1-Dimethylethyl[1S-[[[2-[(2S-amino-1-oxo-3-phenylpropyl)amino]-2-methylpropyl]amino]carbonyl]-2-(4-hydroxy-2,6-dimethylphenyl)ethyl]carbamate, acetic acid salt

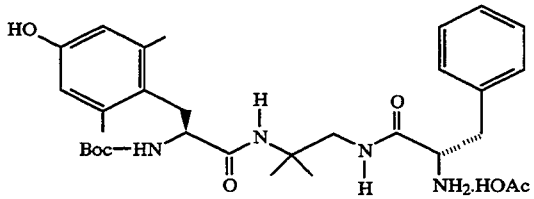

Removal of the benzyloxycarbonyl (Z) protecting group from the product of Example 9 was accomplished by hydrogenation in MeOH, as described in Example 4 above to give a free base. This material was dissolved in HOAc, and the solution was concentrated in vacuo to give the title compound as a white solid.

H$^1$NMR (CD$_3$OD) δ: 2.3 (s, 6H), 6.5 (s, 2H). Calculated for C$_{31}$H$_{46}$N$_4$O$_7$+2 HOAc (MW=646.78): C, 61.28; H, 7.79; N, 8.66. Found: C, 61.36; H, 7.98; N, 8.61. [α]$_D$= +48.3°, MeOH.

Example 12

αS-amino-N-[2-[[2S-amino-3-(4-hydroxy-2,6-dimethylphenyl)-1-oxopropyl]amino]-2-methylpropyl]benzenepropanamide, dihydrochloride

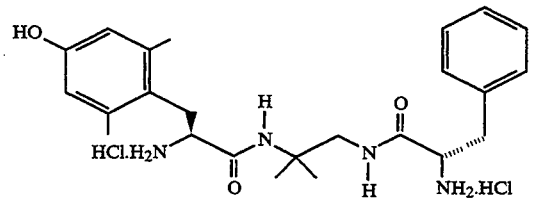

The title compound of Example 11 was treated with HCl by the procedure of Example 3 to give the title compound as a white solid.

H$^1$NMR (CD$_3$OD) δ: 0.9 (s, 3H), 1.2 (s, 3H), 2.3 (s, 6H), 6.5 (s, 6H). Calculated for C$_{24}$H$_{34}$N$_4$O$_3$+2HCl+H$_2$O (MW=517.50): C, 55.70; H, 7.40; N, 10.83; Cl, 13.70. Found: C, 56.00; H, 7.16; N, 10.59; Cl, 13.73. [α]$_D$= +117.6°, MeOH.

Example 13

1,1-Dimethylethyl[1S-[[2-[[1,1-dimethyl-2-[1-oxo-3-phenyl-2S-[(trifluoroacetyl)amino]propyl]amino]ethyl]amino]carbonyl]-2-(4-hydroxy-2,6-dimethylphenyl)ethyl]carbamate

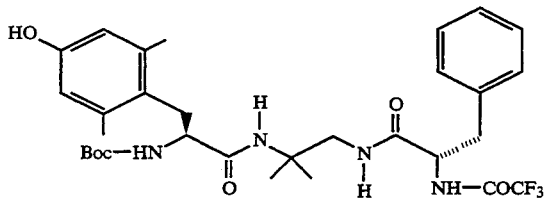

To a stirred solution of the title compound of Example 11 (0.5 g) in CH$_2$Cl$_2$ (25 mL) was added NMM (0.2 g), 4-dimethylamino-pyridine (6 mg) and trifluoroacetic anhydride (0.8 g). After 2 hours, the mixture was washed with 0.5N KHSO$_4$, dried over MgSO$_4$ and concentrated in vacuo. The residue was washed with hexane to leave a white solid. This solid was stirred in methanol (30 mL) and 2.5 mL of 15% aqueous K$_2$CO$_3$ for 16 hours. The mixture was filtered and the filtrate concentrated in vacuo. The residue was dissolved in CH$_2$Cl$_2$ and the solution was washed with water, dried over MgSO$_4$ and concentrated in vacuo to give the title compound as a white solid.

Example 14

αS-Amino-N-[1,1-dimethyl-2-[[1-oxo-3-phenyl-2S-[[tri-fluoroacetyl-amino]propyl]amino]ethyl]-4-hydroxy-2,6-dimethylbenzenepropanamide, hydrochloride

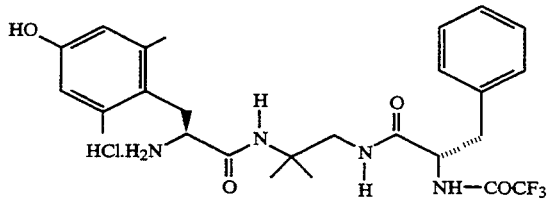

The title compound of Example 13 was treated with HCl by the procedure of Example 3 to give the title compound as a white solid.

H¹NMR (CD₃OH) δ: 0.8 (s, 3H), 1.2 (s, 3H), 2.2 (s, 6H), 6.5 (s, 2H). Calculated for $C_{26}H_{33}F_3N_4O_4 + 1.2$ HCl+0.3 H₂O (MW=571.73): C, 54.62; H, 6.14; N, 9.80; Cl, 7.44. Found: C, 54.64; H, 6.07; N, 9.71; Cl, 7.40. $[\alpha]_D = °85.2°$, MeOH.

Example 15

1,1-Dimethylethyl[1S-[[[2-[[2S-(acetylamino)-1-oxo-3-phenylpropyl]amino]-1,1-dimethylethyl]amino]carbonyl]-2-[4-(acetyloxy)-2,6-dimethylphenyl)]ethyl]carbamate

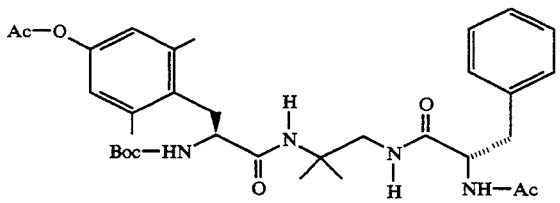

To a stirred solution of the title compound of Example 11 (0.5 g) in CH₂Cl₂ (25 mL) at room temperature and under N₂ was added NMM (0.2 g), 4-dimethylamino-pyridine (6 mg) and acetic anhydride (0.8 g). After 2 hours, the mixture was washed with 0.5N KHSO₄, dried over MgSO₄ and concentrated in vacuo. The residue was washed with hexane to give the title compound as a white solid.

Example 16

αS-(acetylamino)-N-[2-[[3-[4-(acetyloxy)-2,6-dimethyl-phenyl]-2S-amino-1-oxopropyl]amino]-2-methyl-propyl]benzenepropanamide, hydrochloride

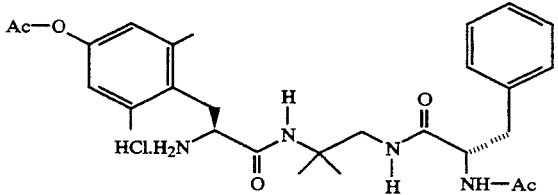

The title compound of Example 15 was treated with HCl by the procedure of Example 3 to give the title compound as a white solid.

H¹NMR (CD₃OD) δ: 0.8 (s, 3H), 1.2 (s, 3H), 1.9 (s, 3H), 2.2 (s, 3H), 2.3 (s, 3H), 6.8 (s, 2H). Calculated for $C_{28}H_{40}N_4O_6 + 1.1$ HCl+H₂O (MW=568.76): C, 59.24; H, 7.12; N, 9.87; Cl, 6.87. Found: C, 59.45; H, 7.12; N, 9.92; Cl, 6.92. $[\alpha]_D = +99.0°$, MeOH.

Example 17

1,1-Dimethylethyl[1S-[[[2-[[2S-(acetylamino)-1-oxo-4-phenylbutyl]amino]-1,1-dimethylethyl]amino]carbonyl]-2-(4-hydroxy-2,6-dimethylphenyl)ethyl] carbamate

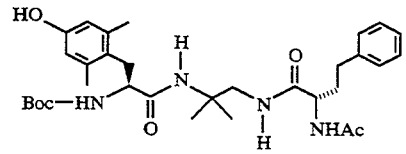

1,2-Diamino-2-methylpropane was coupled to N-acetyl-homophenylalanine and Boc-DMT in succession using the protocol of A. R. Jacobson et al., supra., described in Example 9 above to give the title compound as a white solid.

Example 18

αS-(acetylamino)-N-[2-[[2S-amino-3-(4-hydroxy-2,6-dimethylphenyl)-1-oxopropyl]amino]-2-methylpropyl]-benzenebutanamide, hydrochloride

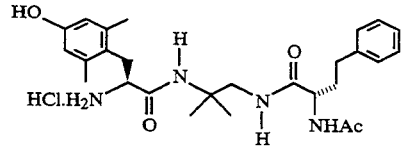

The title compound of Example 17 was treated with HCl by the procedure of Example 3 to give the title compound as a white solid.

H¹NMR (CD₃CO₂D) δ: 0.9 (s, 3H), 1.2 (s, 3H), 2.2 (s, 6H), 6.5 (s, 2H). Calculated for $C_{27}H_{38}N_4O_4 + 1.1$ HCl+1.5 H₂O (MW=549.76): C, 58.99; H, 7.72; N, 10.19; Cl, 7.09. Found: C, 59.01; H, 7.45; N, 10.14; Cl, 7.27. $[\alpha]_D = +44.6°$, MeOH. j

Example 19

1,1-Dimethylethyl[1S-[[[2-[[2S-(acetylamino)-1-oxo-2-phenylethyl]amino]-1,1-dimethylethyl]amino]carbonyl]-2-(4-hydroxy-2,6-dimethylphenyl)ethyl] carbamate

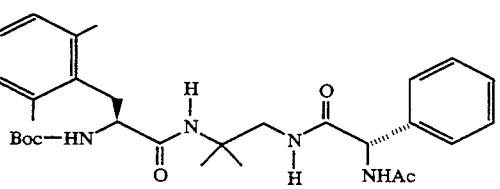

1,2-Diamino-2-methylpropane was coupled to N-acetyl-phenylglycine and Boc-DMT in succession using the protocol of A. R. Jacobson et al., supra., described in Example 9 above to give the title compound as a white solid.

Example 20

N-[2-[[2S-(acetylamino)-2-phenylacetyl]amino]-1,1-dimethylethyl]-αS-amino-4-hydroxy-2,6-dimethylbenzenepropanamide, hydrochloride

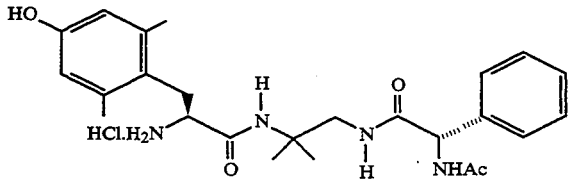

The title compound of Example 19 was treated with HCl by the procedure of Example 3 to give the title compound as a white solid.

H$^1$NMR (CD$_3$CO$_2$D) δ: 0.8 (s, 3H), 1.2 (s, 3H), 2.3 (s, 6H), 6.5 (s, 2H). Calculated for C$_{25}$H$_{34}$N$_4$O$_4$+1.5 HCl+2 H$_2$O (MW=545.30): C, 55.07; H, 7.30; N, 10.27; Cl, 9.75. Found: C, 55.28; H, 6.91; N, 10.10; Cl, 9.59. [α]$_D$= +116.0°, MeOH.

Example 21

Phenylmethyl[1S-[[[2-[[2S-[[(1,1-dimethylethoxy)carbonyl]amino]-3-(4-hydroxy-2,6-dimethylphenyl)-1-oxopropyl]amino]ethyl]amino]carbonyl]-2-phenylethyl] carbamate

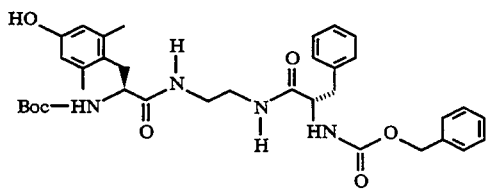

Using 1,2-diamino-ethane in the place of 1,2-diamino-2-methylpropane in the procedure of Example 9, the title compound was obtained as a white solid.

Example 22

Phenylmethyl[1S-[[(2-[[2S-amino-3-[4-hydroxy-2,6-dimethylphenyl)-1-oxopropyl]ethylaminocarbonyl-2-phenylethylcarbamate, monohydrochloride

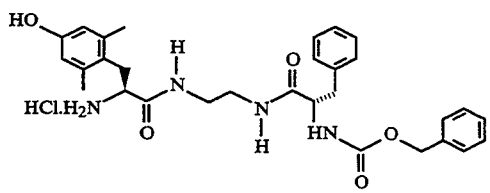

The title compound of Example 21 was treated with HCl by the procedure of Example 3 to give the title compound as a white solid.

H$^1$NMR (CD$_3$OD) δ: 2.3 (s, 6H), 6.5 (s, 2H). Calculated for C$_{30}$H$_{36}$N$_4$O$_5$+1 HCl+0.5 H$_2$O (MW=578.11): C, 62.33; H, 6.63; N, 9.69; Cl, 6.13. Found: C, 62.54; H, 6.60; N, 9.53; Cl, 6.15. [α]$_D$= +77.7°, MeOH.

Example 23

1,1-dimethylethyl[1S-[[[2-[(2S-amino-1-oxo-3-phenylpropyl)amino]ethyl]amino]carbonyl]-2-(4-hydroxy-2,6-dimethylphenyl)ethyl]carbamate, acetate (salt)

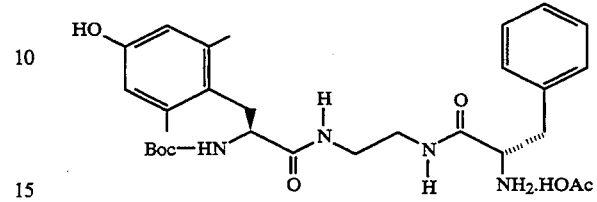

Removal of the Z protecting group from the title compound of Example 21 was accomplished by hydrogenation in methanol as described in Example 4 to give a free base. This material was dissolved in acetic acid and the solution was concentrated in vacuo to give the title compound as a white solid.

H$^1$NMR (CD$_3$OD) δ: 2.2 (s, 6H), 6.5 (s, 2H). Calculated for C$_{29}$H$_{42}$N$_4$O$_7$+1.3 AcOH (MW=576.69): C, 61.65; H, 7.55; N, 9.72. Found: C, 61.59; H, 7.74; N, 9.39. [α]$_D$= +28.4°, MeOH.

Example 24

αS-amino-N-[2-[[2S-amino-3-(4-hydroxy-2,6-dimethylphenyl)-1-oxopropyl]amino]ethyl]-benzenepropanamide, dihydrochloride

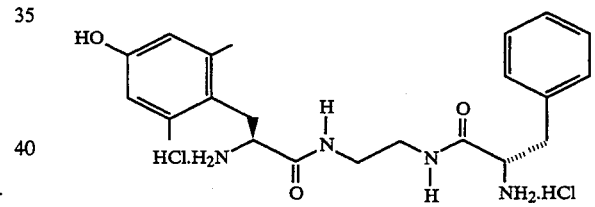

The title compound of Example 23 was treated with HCl by the method of Example 3 to give the title compound as a white solid.

H$^1$NMR (CD$_3$OD) δ; 2.2 (s, 6H), 6.5 (s, 2H). Calculated for C$_{22}$H$_{30}$N$_4$O$_3$+2 HCl+H$_2$O (MW=489.44): C, 53.99; H, 7.00; N, 11.45; Cl, 14.49. Found: C, 53.79; H, 6.83; N, 11.25; Cl, 14.99. [α]$_D$= +72.8°, MeOH.

Example 25

Compound A

Phenylmethyl[1S-[[[2-[[2S-[[(1,1-dimethylethoxy)carbonyl]amino]-3-(4-hydroxy-2,6-dimethylphenyl)-1-oxopropyl]amino]-1,1-dimethylethyl]amino]carbonyl]-2-phenylethyl]carbamate

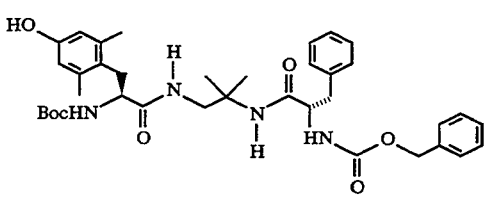

Compound B

Phenylmethyl[1S-[[[2-[[2S-[[(1,1-dimethylethoxy)carbonyl]amino]-3-(4-hydroxy-2,6-dimethylphenyl)-1-oxopropyl]amino]-2-methylpropyl]amino]carbonyl]-2-phenylethyl]carbamate

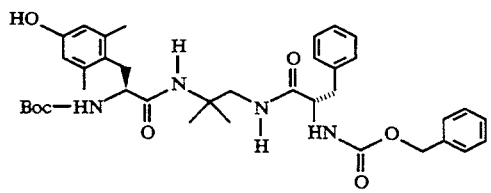

The product mixture of the title compounds of Example 4 was coupled to N-benzyloxycarbonyl-phenylalanine using the mixed anhydride procedure described in Example 2 to give a mixture of the less polar title Compound A and the more polar title Compound B as white solids. Title Compound B is identical to the title compound of Example 9. The isomers were separated by chromatography.

Compound A:

Calculated for $C_{37}H_{48}N_4O_7 + 0.5$ $H_2O$ (MW=669.82): C, 66.35; H, 7.37; N, 8.36. Found: C, 66.30; H, 7.37; N, 8.28. $[\alpha]_D = +38.4°$, $CHCl_3$.

Compound B: Identical to the title compound of Example 9.

Example 26

Phenylmethyl[1S-[[[2-[[2S-amino-3-(4-hydroxy-2,6-dimethylphenyl)-1-oxopropyl]amino]-1,1-dimethylethyl]amino]carbonyl]-2-phenylethyl]carbamate, monohydrochloride

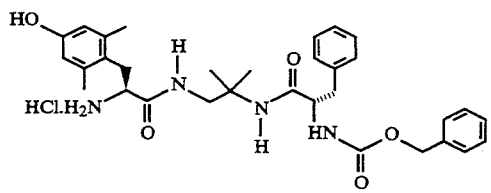

Compound A of Example 25 was treated with HCl by the procedure of Example 3 to give the title compound as a white solid.

$H^1$NMR ($CD_3OD$) δ: 1.02 (s, 3H), 1.03 (s, 3H), 2.25 (s, 6H). Calculated for $C_{32}H_{41}N_4O_5Cl + 0.5$ $H_2O$ (MW=606.16): C, 63.41; H, 6.98; N, 9.24; Cl, 5.85. Found: C, 63.41; H, 6.98; N, 9.24; Cl, 5.85. $[\alpha]_D = +72°$, MeOH.

Example 27

1,1-Dimethylethyl[1S-[[[1,1-dimethyl-2-[[(1-oxo-3-phenyl-2S-[[(2-propenylamino)carbonyl]amino]propyl]amino]ethyl]amino]carbonyl]-2-(4-hydroxy-2,6-dimethylphenyl)ethyl]carbamate

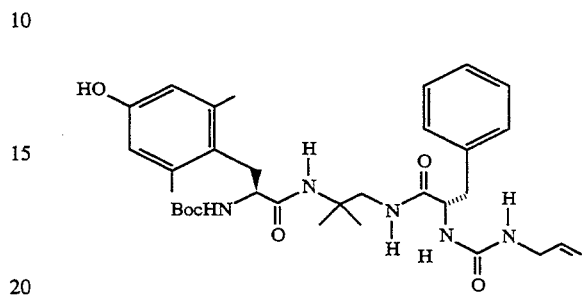

The free base of the title compound of Example 11 was stirred with allylisocyanate in a mixture of benzene (25 mL) and $CH_2Cl_2$ (15 mL) for 18 hours at room temperature. The reaction mixture was washed with 0.5N $KHSO_4$, dried over $MgSO_4$ and concentrated in vacuo. The residue was chromatographed to give the title compound as a white solid. Calculated for $C_{33}H_{47}N_5O_6 + 0.5$ $H_2O$ (MW=618.78): C, 64.06; H, 7.82; N, 11.32. Found: C, 64.07; H, 7.70; N, 11.09. $[\alpha]_D = +21.2°$, $CHCl_3$.

Example 28

αS-amino-N-[1,1-dimethyl-2-[[1-oxo-3-phenyl-2S-[[(2-propenylamino)carbonyl]amino]propyl]amino]ethyl]-4-hydroxy-2,6-dimethylbenzenepropanamide, monohydrochyloride

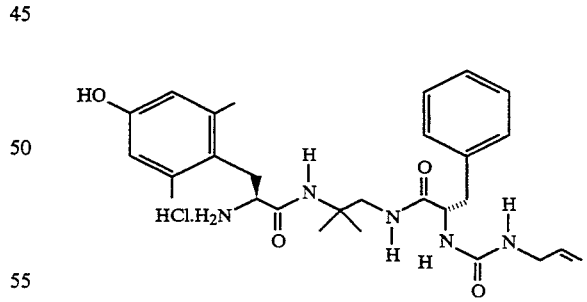

The title compound of Example 27 was treated with HCl by the method of Example 3 to give the title compound as a white solid.

$H^1$NMR ($CD_3OD$) δ: 0.87 (s, 3H), 1.19 (s, 3H), 2.28 (s, 6H). Calculated for $C_{28}H_{39}N_5O_4 + 1.0$ $HCl + 0.5$ $H_2O$ (MW=555.20): C, 60.58; H, 7.44; N, 12.62; Cl, 6.39. Found: C, 60.21; H, 7.44; N, 12.48; Cl, 6.66. $[\alpha]_D = +85.7°$, MeOH.

Example 29

Compound A

Phenylmethyl[1S-[[[2-[[2S-[[(1,1-dimethylethoxy)carbonyl]amino]-3-(4-hydroxy-2,3,6-trimethylphenyl)-1-oxopropyl]amino]-2-methylpropyl]amino]carbonyl]-2-phenylethyl]carbamate

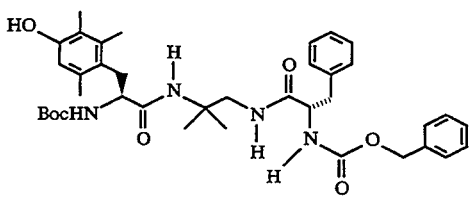

Compound B

Phenylmethyl[1S-[[[2-[[2R-[[(1,1-dimethylethoxy)carbonyl]amino]-3-(4-hydroxy-2,3,6-trimethylphenyl)-1-oxopropyl]amino]-2-methylpropyl]amino]carbonyl]-2-phenylethyl]carbamate

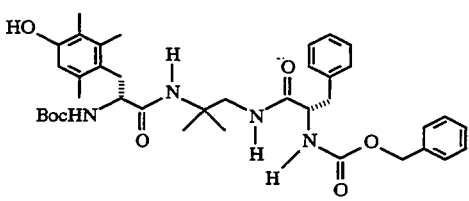

1,2-Diamino-2-methylpropane was coupled to N-benzyloxycarbonyl-L-phenylalanine (Z-Phe) and N-Boc-DL-2,3,6-trimethyltyrosine in succession using the protocol of A. R. Jacobson et al., supra., described above in Example 9. The reaction procedure produced two diastereoisomers which were separated by chromatography. The less polar isomer, title Compound A, and the more polar isomer, title Compound B, were both white solids.

Compound A
Calculated for $C_{38}H_{50}N_4O_7 + 0.125$ $H_2O$ (MW=677.09): C, 67.41; H, 7.48; N, 8.27. Found: C, 67.27; H, 7.71; N, 8.12. $[\alpha]_D = +14.6°$, CHCl$_3$.

Compound B
Calculated for $C_{38}H_{50}N_4O_7 + 0.25$ $H_2O$ (MW=679.34): C, 67.19; H, 7.49; N, 8.25. Found: C, 67.09; H, 7.62; N, 8.15. $[\alpha]_D = -15.4°$, CHCl$_3$.

Example 30

Phenylmethyl[1S-[[[2-[[2S-amino-3-(4-hydroxy-2,3,6-trimethylphenyl)-1-oxopropyl]amino]-2-methylpropyl]amino]carbonyl]-2-phenylethyl]carbamate, hydrochloride

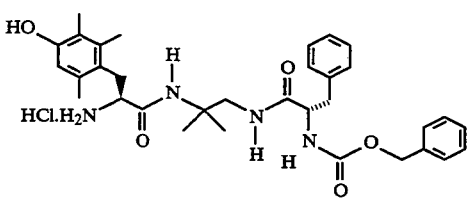

Title Compound A of Example 29 was treated with HCl by the procedure of Example 3 to give the title compound as a white solid.

H$^1$NMR (CD$_3$OD) δ: 0.85 (s, 3H), 1.13 (s, 3H), 2.11 (s, 3H), 2.25 (s, 6H). Calculated for $C_{33}H_{42}N_4O_5 + 1.1$ HCl + 0.25 H$_2$O (MW=619.33): C, 64.00; H, 7.10; N, 9.05; Cl, 6.30. Found: C, 63.89; H, 7.19; N, 8.76; Cl, 6.41. $[\alpha]_D = +46.4°$, MeOH.

Example 31

Phenylmethyl[1S-[[[2-[[2R-amino-3-(4-hydroxy-2,3,6-trimethylphenyl)-1-oxopropyl]amino]-2-methylpropyl]amino]carbonyl]-2-phenylethyl]carbamate, hydrochloride

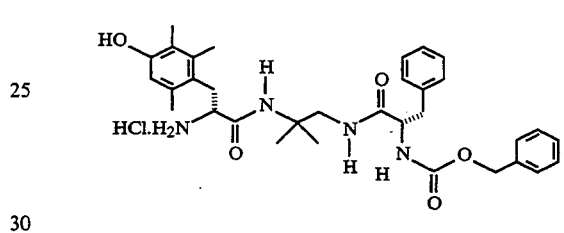

Title Compound B of Example 29 was treated with HCl by the procedure of Example 3 to give the title compound as a white solid.

H$^1$NMR (CD$_3$OD) δ: 0.89 (s, 3H), 1.14 (s, 3H), 2.10 (s, 3H), 2.24 (s, 6H). Calculated for $C_{33}H_{42}N_4O_5 + 1.1$ HCl + 0.25 H$_2$O (MW=619.33): C, 64.00; H, 7.10; N, 9.05; Cl, 6.30. Found: C, 64.09; H, 7.29; N, 9.00; Cl, 6.37. $[\alpha]_D = -58.7°$, MeOH.

Example 32

1,1-Dimethylethyl[1S-[[[1,1-dimethyl-2-[[(1-oxo-3-phenyl-2S-[[[(phenylmethyl)amino]carbonyl]amino]propyl]amino]ethyl]amino]carbonyl]-2-(4-hydroxy-2,6-dimethylphenyl)ethyl]carbamate

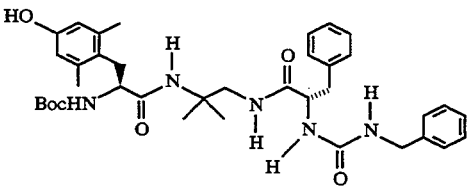

The free base of the title compound of Example 11 was treated with benzylisocyanate by the method of Example 27 to give the title compound as a white solid.

Calculated for $C_{37}H_{49}N_5O_6$ (MW=659.86): C, 67.35; H, 7.49; N, 10.61. Found: C, 67.05; H, 7.58; N, 10.57. $[\alpha]_D = -6.3°$, CHCl$_3$.

Example 33

αS-amino-N-[1,1-dimethyl-2-[[1-oxo-3-phenyl-2S-[[[(phenylmethyl)amino]carbonyl]amino]propyl]amino]ethyl]-4-hydroxy-2,6-dimethylbenzenepropanamide, hydrochloride

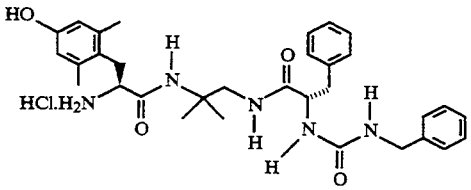

The title compound of Example 32 was treated with HCl by the procedure of Example 3 to give the title compound as a white solid.

H¹NMR (CD₃OD) δ: 0.85 (s, 3H), 1.20 (s, 3H), 2.26 (s, 6H). Calculated for $C_{32}H_{41}N_5O_4 + 1.1$ HCl+0.5 H₂O (MW=608.83): C, 63.13; H, 7.14; N, 11.50; Cl, 6.41. Found: C, 63.22; H, 7.14; N, 11.36; Cl, 6.40. $[\alpha]_D = +72.3°$, MeOH.

Example 34

Ethyl[[[[1S-[[[2-[[2S-[[(1,1-dimethylethoxy)carbonyl]amino]-3-(4-hydroxy-2,6-dimethylphenyl)-1-oxopropyl]amino]-2-methylpropyl]amino]carbonyl]-2-phenylethyl]amino]carbonyl]amino]acetate

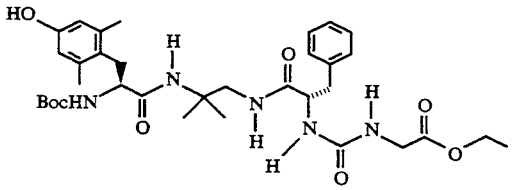

The free base of the title compound of Example 11 was treated with ethyl isocyanatoacetate by the method of Example 27 to give the title compound as a white solid.

Calculated for $C_{34}H_{48}N_5O_8 + 0.2$ H₂O (MW=658.39): C, 62.03; H, 7.41; N, 10.64. Found: C, 61.67; H, 7.46; N, 10.48. $[\alpha]_D = -8.5°$, CHCl₃.

Example 35

αS-amino-N-[1,1-dimethyl-2-[[1-oxo-3-phenyl-2S-[[[(phenylmethyl)amino]carbonyl]amino]propyl]amino]ethyl]-4-hydroxy-2,6-dimethylbenzenepropanamide, hydrochloride

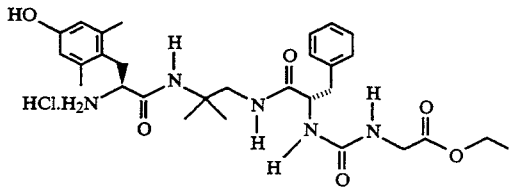

The title compound of Example 34 was treated with HCl by the procedure of Example 3 to give the title compound as a white solid.

H¹NMR (CD₃OD) δ: 0.87 (s, 3H), 1.18 (s, 3H), 2.28 (s, 6H). Calculated for $C_{29}H_{40}N_5O_6 + 1.1$ HCl+0.4 H₂O (MW=601.98): C, 57.86; H, 7.02; N, 11.63; Cl, 6.48. Found: C, 57.86; H, 7.12; N, 11.44; Cl, 6.31. $[\alpha]_D = +79.4°$, MeOH.

Example 36

1,1-Dimethylethyl[1S-[[[1,1-dimethyl-2-[[[(1-oxo-3-phenyl-2S-[[(methylamino)carbonyl]amino]propyl]amino]ethyl]amino]carbonyl]-2-(4-hydroxy-2,6-dimethylphenyl)ethyl]carbamate

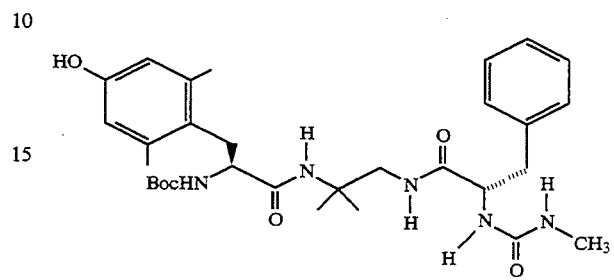

The free base of the title compound of Example 11 was treated with methyl isocyanate by the method of Example 27 to give the title compound as a white solid.

Calculated for $C_{31}H_{48}N_5O_6 + 0.9$ H₂O (MW=519.26): C, 62.06; H, 7.86; N, 11.67. Found: C, 61.96; H, 7.65; N, 11.52. $[\alpha]_D = +4.5°$, CHCl₃.

Example 37

αS-amino-N-[1,1-dimethyl-2-[[2S-[[(methylamino)carbonyl]amino]-1-oxo-3-phenylpropyl]amino]ethyl]-4-hydroxy-2,6-dimethylbenzenepropanamide, monohydrochloride

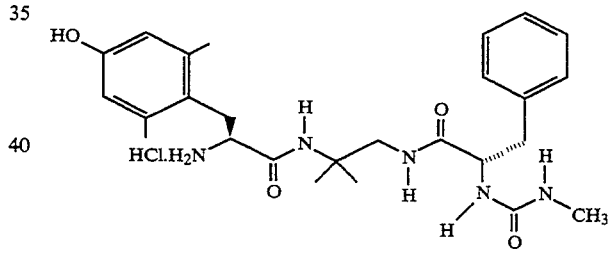

The title compound of Example 36 was treated with HCl by the procedure of Example 3 to give the title compound as a white solid.

H¹NMR (CD₃OD) δ: 0.87 (s, 3H), 1.18 (s, 3H), 2.28 (s, 6H). Calculated for $C_{26}H_{37}N_5O_4 + 1.0$ HCl+0.75 H₂O (MW=533.59): C, 58.53; H, 7.46; N, 13.13; Cl, 6.64. Found: C, 58.61; H, 7.54; N, 12.64; Cl, 6.30. $[\alpha]_D = +87.0°$, MeOH.

Example 38

1,1-Dimethylethyl[1S-[[[2-[[2S-(acetylamino)-1-oxo-3-phenylpropyl]amino]-2-methylpropyl]amino]carbonyl]-2-(4-hydroxy-2,6-dimethylphenyl)ethyl]carbamate

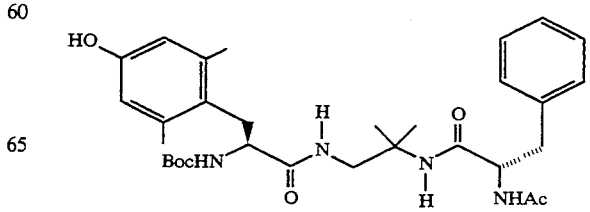

Removal of the benzyloxycarbonyl (Z) group from title Compound A of Example 25 was accomplished by the method of Example 4 to give a free base. This free base was then converted to the white solid title compound by the process of Example 13, with the exception that acetic anhydride was used in place of trifluoroacetic anhydride.

Calculated for $C_{31}H_{44}N_5O_6 + 0.6$ $H_2O$ (MW=579.52): C, 64.25; H, 7.86; N, 9.67. Found: C, 64.02; H, 7.74; N, 9.48. $[\alpha]_D = +45.8°$, CHCl$_3$.

Example 39

αS-(Acetylamino)-N-[2-[[2S-amino-3-(4-hydroxy-2,6-dimethylphenyl)-1-oxopropyl]amino]-1,1-dimethylethyl]benzenepropanamide, monohydrochloride

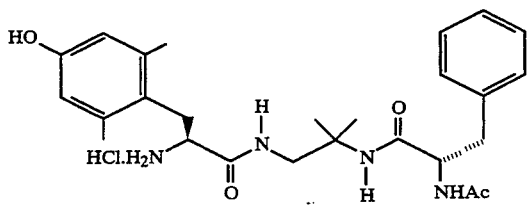

The title compound of Example 38 was treated with HCl by the procedure of Example 3 to give the title compound as a white solid.

H$^1$NMR (CD$_3$OD) δ: 1.01 (s, 3H), 1.04 (s, 3H), 2.25 (s, 6H). Calculated for $C_{26}H_{36}N_4O_4 + 1.0$ HCl + 0.75 $H_2O$ (MW=518.57): C, 61.83; H, 7.38; N, 11.09; Cl, 7.02. Found: C, 60.22; H, 7.42; N, 10.80; Cl, 6.84. $[\alpha]_D = +102.9°$, MeOH.

Example 40

1,1-Dimethylethyl[1R-[[[2-[[2S-(acetylamino)-1-oxo-3-phenylpropyl]amino]-1,1-dimethylethyl]amino]carbonyl]2-(4-hydroxy-2,3,6-trimethylphenyl)ethyl]carbamate

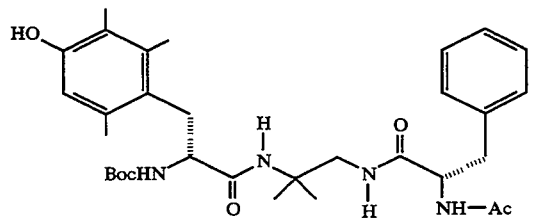

Removal of the Z group from title Compound A of Example 29 was accomplished by the method of Example 4 to give a free base. This free base was then converted to the white solid title compound by the process of Example 13, with the exception that acetic anhydride was used in place of trifluoroacetic anhydride.

Calculated for $C_{32}H_{46}N_4O_6 + 0.25$ $H_2O$ (MW=587.25): C, 65.45; H, 7.98; N, 9.54. Found: C, 65.46; H, 8.09; N, 9.12. $[\alpha]_D = -40.0°$, CHCl$_3$.

Example 41

αS-(acetylamino)-N-[2-[[2R-amino-3-(4-hydroxy-2,3,6-trimethylphenyl)-1-oxopropyl]amino]-2-methylpropyl]-benzenepropanamide, monohydrochloride

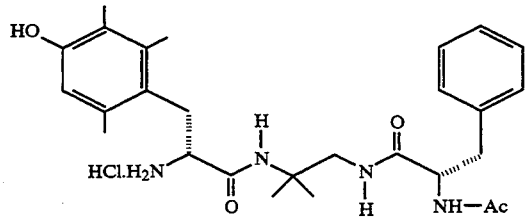

The title compound of Example 40 was treated with HCl by the procedure of Example 3 to generate the title compound as a white solid.

H$^1$NMR (CD$_3$OD) δ: 0.90 (s, 3H), 1.14 (s, 3H), 1.91 (s, 3H), 2.23 (s, 6H). Calculated for $C_{27}H_{38}N_4O_4 + 1.0$ HCl + 0.5 $H_2O$ (MW=528.10): C, 62.48; H, 7.57; N, 10.79; Cl, 6.83. Found: C, 61.41; H, 7.63; N, 10.61; Cl, 6.71. $[\alpha]_D = -49.0°$, MeOH.

Example 42

1,1-Dimethylethyl[(1R-methyl-2-[(phenylmethyl)amino]ethyl]carbamate

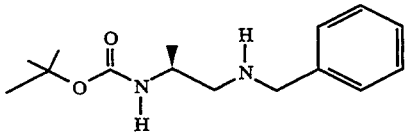

t-Butyloxycarbonyl-D-alanine (Boc-D-Ala) was coupled to benzylamine using the mixed anhydride method described in Example 2 to give the white solid Boc-D-Ala-NH$_2$-CH$_2$-phenyl, which was used without further purification. To a stirred solution of 10 g of this material in 75 mL of THF at −20° C. was added 72 mL of a 1M THF solution of borane in drops. The mixture was allowed to stir for 6.5 hours at −20° C. To this mixture was added 40 mL of MeOH in drops. The mixture was concentrated in vacuo. The residue was treated with 50 mL of MeOH and the volatiles were removed in vacuo. This process of addition of MeOH and concentration was repeated three times. The residue was suspended in 400 mL of water and acidified to pH=2 with concentrated hydrochloric acid. The solution was extracted with ether. The organic phase was discarded. The aqueous phase was basified with saturated aqueous K$_2$CO$_3$ and extracted with ether. The ether extract was dried over MgSO$_4$ and concentrated in vacuo to leave 1.04 g of the title compound, which was used in Example 53 without further purification.

Example 43

1,1-Dimethylethyl(2-amino-1R-methylethyl)carbamate

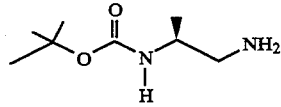

The title compound of Example 42 (0.912 g) was hydrogenated in MeOH (25 mL) with 10% Pd on carbon under 60 psi hydrogen pressure for 22 hours. The reaction was worked up as described in Example 4 to give the title compound (0.595 g) as a white solid.

Example 44

1,1-Dimethylethyl[(1R-methyl-2-[(phenylmethyl)amino]ethyl]carbamate

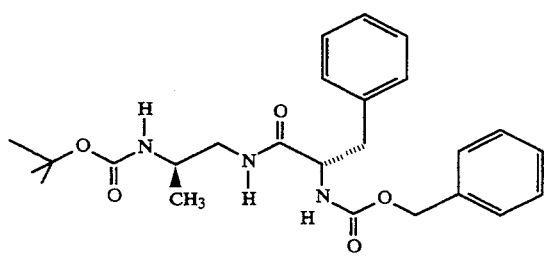

The title compound of Example 43 was coupled to Z-Phe by the method of Example 2 to give the title compound as a white solid.

Example 45

Phenylmethyl[1S-[[[2R-[[2S-[[(1,1-dimethylethoxy)carbonyl]amino]-3-(4-hydroxy-2,6-dimethylphenyl)-1-oxopropyl]amino]propyl]carbonyl]-2-phenylethyl]carbamate

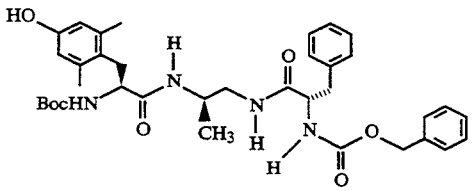

The title compound of Example 44 was treated with HCl by the method of Example 3. The resulting amine hydrochloride salt was treated with a molar equivalent of NMM and then coupled to Boc-DMT using the mixed anhydride coupling procedure of Example 2 to give the title compound as white solid.
Calculated for $C_{36}H_{46}N_4O_7 + 0.25$ $H_2O$ (MW=651.29): C, 66.39; H, 7.20; N, 8.60. Found: C, 66.33; H, 7.23; N, 8.37. $[\alpha]_D = +12.8°$, $CHCl_3$.

Example 46

Phenylmethyl[1S-[[[2R-[[2S-amino-3-(4-hydroxy-2,6-dimethylphenyl)-1-oxopropyl]amino]propyl]amino]carbonyl-2-phenylethyl]carbamate, hydrochloride

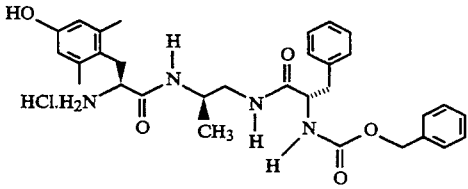

The title compound of Example 45 was treated with HCl by the method of Example 3 to give the title compound as a white solid.
H¹NMR (CD₃OD) δ: 0.72 (d, 3H), 2.23 (s, 6H). Calculated for $C_{31}H_{38}N_4O_5 + 0.9$ HCl + 0.5 $H_2O$ (MW=588.49): C, 63.85; H,6.74; N, 9.61; Cl, 6.08. Found: C, 63.27; H, 6.83; N, 9.54; Cl, 5.42. $[\alpha]_D = +45.9°$, MeOH.

Example 47

αS-(Acetylamino)-N-[2-[[2S-amino-3-(4-hydroxy-2,6-dimethylphenyl)-1-oxopropyl]amino]-2-methylpropyl]-benzenepropanamide, monohydrochloride

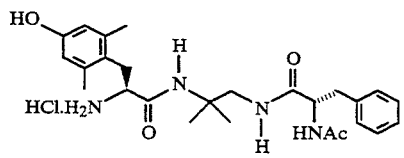

To $CH_2Cl_2$ (70 mL) at 0° C. was added 3.9 g of Boc-DMT, 3.5 g of N-acetyl-phenylalanine-NHCHC(CH₃)₂NH₂ of A. R. Jacobson et al., supra., and 1.7 g of hydroxybenzotriazole (HOBT). After stirring for 5 minutes, 2.86 g of dicyclohexylcarbodiimide (DCC) was added. The reaction mixture was allowed to warm to room temperature overnight with stirring. After filtration, the mother liquor was washed with two 100 mL portions of half-saturated $Na_2CO_3$ and evaporated to dryness in vacuo. The crude product obtained was treated with a 1:1 mixture of 15 mL of $CH_2Cl_2$ and 7N HCl in dioxane for 5 minutes at room temperature to remove the Boc protecting group. The volatiles were removed and the residue was purified by chromatography over silica gel using a mobile phase of $CHCl_3$/MeOH (8:1) containing 1% aqueous $NH_3$ to give the free base of the title compound. Treatment of an ethanol solution of this free base with dry HCl gas and removing the volatiles in vacuo gave the title compound as a white solid.
H¹NMR (D₂O) δ: 0.90 (s, 3H), 1.0 (s, 3H), 1.98 (s, 3H), 2.18 (s, 3H), 2.92–3.25 (complex m, 6H), 3.89 (dd, J=10, 7 Hz, 1H), 4.43 (t, J=7.5, 1H), 6.68 (s, 2H), 7.22–7.43 (complex m, 5H). HPLC (Zorbax-Rx-C-8, 17/83 acetonitrile/TEAP (triethylamine-phosphate buffer, pH=3)) =15.3 $[\alpha]_D = +80.6$ (MeOH)

Example 48

αS-(Acetylamino)-N-[2-[[2S-amino-3-(4-hydroxy-2,6-dimethylphenyl)-1-oxopropyl]amino]ethyl]benzenepropanamide, hydrochloride

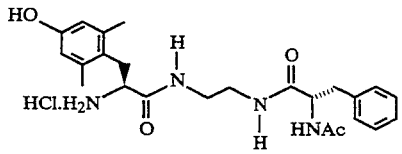

To 100 mL of DMF was added N-acetyl-phenylalanine [N-Ac-PheOH (Aldrich, Milwaukee, Wis.), 5 g], 1.61 mL of ethylenediamine, 4.6 g of para-toluenesulfonic acid. $H_2O$ and 3.3 g of HOBT. After allowing the mixture to stir for 5 minutes, 5.1 g of DCC was added and the reaction mixture was stirred for 16 hours. The solvent was removed in vacuo and 500 mL of $CHCl_3$ was added. The mixture was filtered and the filtrate was washed with two 200-mL portions of half-saturated aqueous $Na_2CO_3$. The organic extract was concentrated in vacuo. The residue was chromatographed on silica gel using EtOAc/MeOH (4:1) containing 1% aqueous NH₃ to give 1.5 g of white solid, H₂N(CH₂)₂NH-phenylalanine-NH-acetyl.

To a solution of 1.723 g of Boc-DMT in 50 mL of THF at −10° C. was added 0.615 mL of N-methylmorpholine (NMM) followed by 0.725 mL of isobutylchloroformate (IBCF). The mixture was stirred for 30 minutes. To this mixture was added 1.342 g of H₂N(CH₂)₂NH-phenylalanine-NH-acetyl in 20 mL of DMF. The mixture was stirred and allowed to warm to room temperature over 16 hours. The mixture was concentrated and the residue was taken up in EtOAc and water. The organic phase was washed with 0.5N KHSO₄, saturated NaHCO₃, dried over MgSO₄ and concentrated in vacuo. The residue was chromatographed on silica using EtOAc containing 1% MeOH. The white solid obtained was taken up in 10 mL of CH₂Cl₂ and 7N HCl in dioxane (1:1) and allowed to stand at room temperature for 5 minutes. The volatiles were removed and the residue was chromatographed over silica gel using CHCl₃/MeOH (8:1) containing 1% aqueous NH₃ to give 1 g of the free base of the title compound. The title compound was obtained as a white solid salt by dissolving the free base in EtOH containing dry HCl and azeotropic drying.

H¹NMR (DMSO-d₆) δ: 1.76 (s, 3H), 2.18 (s, 6H), 2.70–3.08 (complex m, 8H), 3.63 (m, 1H), 4.36 (m, 1H), 6.43 (s, 2H), 7.16–7.29 (complex m, 5H), 8.09 (bs, 2H), 8.21 (d, J=8 Hz, 1H), 8.56 (bs, 3H), 9.12 (very bs, 1H). HPLC (Zorbax-Rx-C-8, 30/70 to 90/10 for 20 minutes, 90/10 for 5 minutes, methanol/TEAP)=8.97 [α]_D= +109.0 (MeOH)

Example 49

N-Acetyl-2,6-dimethyl-L-phenylalanine, methyl ester

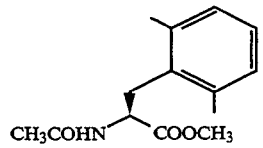

A mixture of 3,5-dimethyl-4-iodophenyl acetate (175 g, 603 mmol), methyl 2-acetamidoacrylate (90.6 g, 633 mmol), tri-o-tolylphosphine (9.70 g, 31.9 mmol), Et₃N (167 mL, 121 g, 1.20 mol) and palladium(II) acetate (2.51 g, 11.2 mmol) in CH₃CN (850 mL) was refluxed for 22 hours. The mixture was cooled to room temperature and filtered through a bed of Super-Cel. The solvent was removed in vacuo and the residue was diluted with water (1 L). The aqueous phase was extracted three times with EtOAc (4 L total). The organic phase was washed with a saturated NaCl solution (3 L total), treated with Darco ®, and dried over anhydrous Na₂SO₄. The mixture was filtered and concentrated in vacuo. Recrystallization from 25% EtOAc/75% hexane (~3 L total) afforded methyl 2-(acetylamino)-3-[4-(acetyloxy)-2,6-dimethylphenyl]-2Z-propanoate (156 g, 84.7%).

An N₂-purged reaction vessel was charged with a slurry of Rhodium 1,5-cyclooctadiene[R,R]-1,2-ethanediyl bis[[o-methoxyphenyl]phenylphosphine]tetrafluoroborate (35.5 g, 47.0 mmol, methyl 2-(acetylamino)-3-[4-(acetyloxy)-2,6-dimethylphenyl]-2Z-propanoate (1.43 kg, 4.68 mol) and EtOAc (7.2 L) using additional EtOAc (7.2 L) as a rinse. The reaction mixture was heated to 60° C. and repeatedly pressurized to 60 psig with N₂ and vented to 10 psig until the vent stream contained <5 ppm of O₂, as measured by a Teledyne O₂ analyzer. The reaction vessel was then purged five times by pressurizing to 60 psig with H₂ and venting to 10 psig. The vent stream was again checked to ensure that it contained <5 ppm of O₂. The reaction mixture was pressurized to 60 psig with H₂ and stirred vigorously for 24 hours, at which time TLC analysis (60% EtOAc/40% toluene) indicated the complete disappearance of starting material. The reaction mixture was cooled to 25° C., vented with N₂, and added to a second reaction vessel containing Florisil ® (2.15 kg) using EtOAc (4 L) as a rinse. The mixture was filtered through a bed of Super-Cel, and the bed was washed with EtOAc (4.3 L). Approximately ¾ of the solvent was removed by vacuum distillation at 40° C. The resulting slurry was cooled to 25° C. and diluted with hexane (21.5 L). The product was collected by filtration, washed with hexane (5.7 L), and dried to give N-acetyl-2,6-dimethyl-L-tyrosine methyl ester (1.25 kg, 86.7%) as a crystalline solid, DSC 112.25° C. (max endotherm), 200 MHz ¹H (CDCl₃) δ1.97 (s, 3H), (s, 3H), 2.33 (s, 6H), 3.03 (dd, J=8.5 Hz, J=14 Hz, 1H), 3.12 (dd, J=7.5 Hz, J=14 Hz, 1H), 3.60 (s, 3H), 4.79 (q, J=8, 1H), 6.11 (br d, J=8 Hz, 1H), 6.75 (s, 2H); Analysis calculated for C₁₆H₂₁NO₅: C, 62.53; H, 6.89; N, 4.56; Found C, 62.42; H, 7.11; N, 4.53.

A mixture of 10 g of N-acetyl-2,6-dimethyl-L-tyrosine methyl ester and 5 g of NaHCO₃ in 100 mL of MeOH and 10 mL of water was stirred at room temperature for 16 hours. The mixture was acidified with 1N HCl and extracted with ether. The ether extract was washed with water, dried over MgSO₄ and concentrated in vacuo to leave 7 g of N-acetyl-2,6-dimethyl-tyrosine methyl ester as a white solid. 6.87 g of this material was stirred with 4.75 g of 5-chloro-2-phenyl-1H-tetrazole and 7.2 g of K₂CO₃ in 130 mL of DMF for 16 hours. The mixture was added to water and extracted with EtOAc. The organic extract was washed four times with water, dried over MgSO₄ and concentrated. The residue was triturated with ether and filtered to give 7.89 g of a solid [H¹NMR (CDCl₃) δ: 2.00 (s, 3H), 2.20 (s, 6H), 3.04–3.18 (complex, 2H), 3.65 (s, 3H), 4.83 (q, J=8 Hz, 1H), 6.25 (d, J=8 Hz, 1H), 7.06 (s, 2H), 7.49–7.63 (complex, 3H), 7.80 (d, J=8 Hz, 2H)]. This material in 100 mL of HOAc was shaken with 10% Pd on carbon under 60 psi of hydrogen pressure at 40° C. for 24 hours. The mixture was filtered and the filtrate was concentrated in vacuo. The residue was extracted with EtOAc and water. The organic phase was washed with saturated NaHCO₃, water, dried over MgSO₄ and concentrated in vacuo. The residue was triturated with ether and filtered to give 4.48 g of the title compound as a white solid. H¹NMR (CDCl₃) δ: 2.00 (s, 3H), 2.37 (s, 6H), 3.13 (d, J=8 Hz, 2H), 3.63 (s, 3H), 4.87 (q, J=8 Hz, 1H), 6.37 (d, J=8 Hz, 1H), 7.00–7.10 (complex, 3H). [α]_D= +14.5 (MeOH)

Example 50

N-Acetyl-2,6-dimethyl-L-phenylalanine

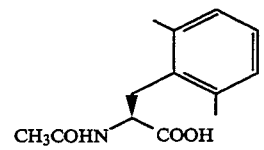

The title compound of Example 49 (4.44 g) was stirred in 19 mL of THF and 18.8 mL of 1M lithium hydroxide for 15 minutes. The volatiles were removed in vacuo and diluted with water. Acidification with 0.5N KHSO$_4$ precipitated a white solid which was filtered and dried in vacuo at 56° C. for 16 hours to give 3.9 g of the title compound as a white solid.

H$^1$NMR (CDCl$_3$-CD$_3$OD) δ: 1.93 (s, 3H), 2.37 (s, 6H), 3.06 (dd, J=14, 8 Hz, 1H), 3.21 (dd, J=14, 7 Hz, 1H), 4.74 (dd, J=8, 7 Hz, 1H), 6.97–7.06 (complex, 5H). [α]$_D$= +29.3 (MeOH)

Example 51

αS-(Acetylamino)-N-[2-[[2S-amino-3-(4-hydroxyphenyl)-1-oxopropyl]amino]ethyl]-2,6-dimethylbenzenepropanamide, hydrochloride

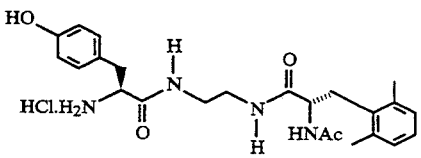

The title compound was obtained as a white solid by the method of Example 48 using the title compound of Example 50 and Boc-tyrosine in place of N-Ac-PheOH and Boc-DMT respectively.

H$^1$NMR (DMSO-d$_6$) δ: 1.80 (s, 3H), 2.29 (s, 6H), 2.78–3.07 (complex, 8H), 3.82 (m, 1H), 4.43 (q, J=8 Hz, 1H), 6.71 (d, J=8 Hz, 2H), 6.89–6.98 (complex, 3H), 7.02 (d, J=8 Hz, 2H), 7.91 (t, J=5 Hz, 1H), 8.24 (bs, 3H), 8.32 (d, J=8 Hz, 1H), 8.48 (m, 1H), 9.37 (very bs, 1H). HPLC (Zorbax-Rx-C-8, 15/85, MeOH/TEAP)=10.90 [α]$_D$= +107.5 (c=2, MeOH)

Example 52

αS-(Acetylamino)-N-[2-[[2S-amino-3-(4-hydroxy-2,6-dimethylphenyl)-1-oxopropyl]amino]ethyl]-2,6-dimethylbenzenepropanamide, hydrochloride

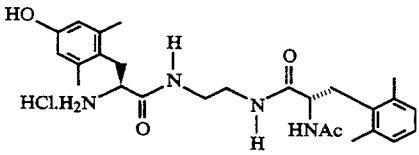

The title compound was obtained as a white solid by the method of Example 48 using the title compound of Example 50 in place of N-Ac-PheOH.

H$^1$NMR (DMSO-d$_6$) δ: 1.80 (s, 3H), 2.16 (s, 6H), 2.28 (s, 6H), 2.53–3.04 (complex, 8H), 3.59 (m, 1H), 4.39 (q, J=7.5 Hz, 1H), 6.43 (s, 2H), 6.90–7.01 (m, 3H), 7.77–7.84 (m, 1H), 7.99 (t, J=5 Hz, 1H), 8.26 (d, J=8 Hz, 1H), 8.30 (bs, 1H), 9.14 (very bs, 1H). HPLC (Zorbax-Rx-C-8, 30/70 to 90/10 for 20 minutes, 90/10 for 5 minutes, methanol/TEAP)=11.86 [α]$_D$= +134.9 (MeOH)

Example 53

1-[2S-Amino-3-(4-hydroxy-2,6-dimethylphenyl)-1-oxopropyl]-4-(phenylmethyl)piperazine, dihydrochloride

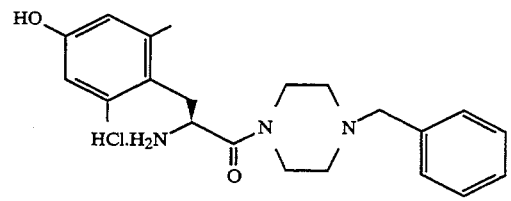

To a solution of 2 g of Boc-DMT in 25 mL of THF at −23° C. was added 0.71 mL of NMM followed by 0.84 mL of IBCF. The mixture was stirred for 30 minutes. To this was added a solution of 1.13 mL of N-benzylpiperazine in 5 mL of THF. The mixture was stirred for 16 hours and concentrated in vacuo. The residue was taken up in EtOAc and water. The organic phase was washed with saturated Na$_2$CO$_3$, dried over MgSO$_4$ and concentrated in vacuo. The residue was chromatographed on silica gel using 60% EtOAc in hexane containing 2% triethylamine to give 3 g of a white solid (Compound A, the Boc precursor of the title compound). 0.2 g of this solid was dissolved in a mixture of 5 mL each of CH$_2$Cl$_2$ and 7N HCl in dioxane. The solution was allowed to stand at room temperature for 15 minutes. The volatiles were removed in vacuo to give the title compound as a white solid. HPLC (Zorbax-Rx-C-8, 30/70 to 90/10 for 20 minutes, 90/10 for 5 minutes, methanol/TEAP)=11.21 [α]$_D$= +48.2 (MeOH)

Example 54

N-[1S-[[4-[2S-Amino-3-(4-hydroxy-2,6-dimethylphenyl)-1-oxopropyl]-1-piperazinyl]carbonyl]-2-phenylethyl]acetamide, monohydrochloride

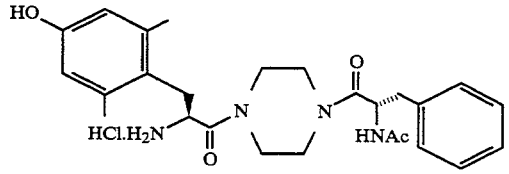

2.4 g of the Boc precursor of the title compound of Example 53 was shaken in 100 mL of EtOH with 5% Pd on carbon under 60 psi of hydrogen for 8 hours. The mixture was filtered to remove the catalyst and the filtrate was concentrated to give 1.3 g of white solid. This material was coupled to N-acetyl-L-phenylalanine using the mixed anhydride coupling procedure described in the preparation of the title compound of Example 53. The crude product was treated with acid to remove the Boc protecting group as described in the preparation of the title compound of Example 47. The crude amine hydrochloride obtained was chromatographed over silica gel using EtOAc/triethylamine/MeOH (98/2/5) to give 0.2 g of the free amine corresponding to the title compound which was converted to the hydrochloride salt by the method described for the title compound of Example 47. HPLC (Zorbax-Rx-C-8, 30/70 to 90/10 for 20 minutes, 90/10 for 5 minutes, methanol/TEAP)=9.70 [α]$_D$= +53.5 (MeOH)

Example 55

1,1-Dimethylethyl[1S-[[[1-[2S-(acetylamino)-1-oxo-3-phenylpropyl]-3-pyrrolidinyl]amino]carbonyl]-2-(4-hydroxy-2,6-dimethylphenyl)ethyl]carbamate

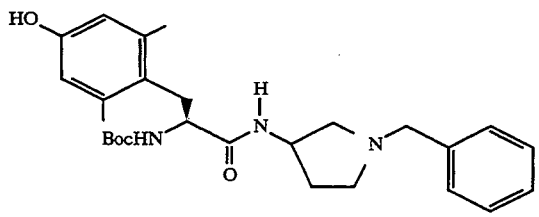

1-Benzyl-3-amino-pyrrolidine was used in the place of 1-benzylpiperazine in the mixed anhydride procedure of Example 53 to give the title compound as a white solid.

Example 56

N-[1-[2S-(Acetylamino)-1-oxo-3-phenylpropyl]-3-pyrrolidinyl]-αS-amino-4-hydroxy-2,6-dimethylbenzenepropanamide, monohydrochloride

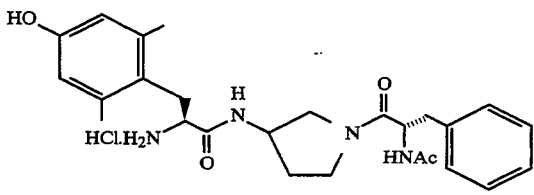

The title compound of Example 55 was subjected to hydrogenation and the resulting product was reacted with N-Ac-L-PheOH as described in Example 54. Subsequent removal of the Boc protecting group as described in Example 54 gave the title compound as a white solid. HPLC (VYOAC-C-18, 90/10 acetonitrile/TEAP)=18.49. $[\alpha]_D = +116.8$ (MeOH)

Example 57

αS-(Acetylamino)-N-[3[[[2S-amino-3-[4-hydroxy-2,6-dimethylphenyl]-1-oxopropylamino]phenyl]benzenepropanamide, hydrochloride

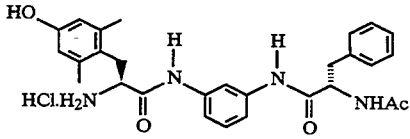

To a solution of 2.06 g of Boc-DMT in 50 mL of THF at −23° C. was added 0.73 mL of NMM followed by 0.86 mL of IBCF. The mixture was stirred for 30 minutes and treated with 0.92 g of m-nitroaniline in 10 mL of THF. The resulting mixture was stirred for four days at room temperature. The volatiles were removed in vacuo. The reaction mixture was worked up as described in Example 53. The crude product obtained was triturated with ether to give 2.7 g of a solid. 1.2 g of this solid was hydrogenated in MeOH with 4% Pd on carbon under 5 psi of hydrogen pressure for 16 hours. The mixture was filtered to remove the catalyst and the filtrate was concentrated in vacuo to leave 1 g of a solid. This material was treated with the mixed anhydride obtained from 0.576 g of N-Ac-L-PheOH, 0.28 mL of NMM and 0.33 mL of IBCF in 25 mL of THF using the procedure described in Example 48. The product obtained was treated with acid to remove the BOC protecting group as described for Example 47. After the removal of the volatiles, the resulting material was chromatographed over silica gel using EtOAC/MeOH/triethyl amine, 50:2:1, to give the free base of the title compound. This material was taken up in acetic acid and dry HCl (gas) was bubbled for a few minutes. The volatiles were removed and the residue was dried in vacuo at 60° C. for 16 hours to give the title compound as a white solid.

H¹NMR (DMSO-d$_6$) δ: 1.80 (s, 3H), 2.20 (s, 6H), 2.83 (dd, J=14, 10 Hz, 1H), 2.96–3.17 (complex, 3H), 3.93 (m, 1H), 4.53 (m, 1H), 6.34 (s, 2H), 7.17–7.33 (9H), 7.74 (bs, 1H), 8.32 (d, J=8 Hz, 1H), 8.63 (bs, 3 H), 9.09 (bs, 1H), 9.98 (s, 1H), 10.2 (s, 1H). HPLC (Zorbax-Rx-C-8, 30/70 to 90/10 for 20 minutes, 90/10 for 5 minutes, methanol/TEAP)=11.72. $[\alpha]_D = +187.7$ (MeOH)

Example 58

1,1-Dimethylethyl-[2-[[1,1-dimethyl-2-[[1-oxo-3-phenyl-2S-[[[(phenylsulfonyl)amino]carbonyl]amino]propyl]amino]ethyl]amino]-1S-[(4-hydroxy-2,6-dimethylphenyl)methyl-2-oxoethyl]-carbamate

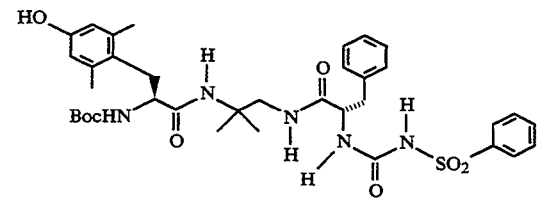

The free base of the title compound of Example 11 was treated with benzenesulfonyl isocyanate by the procedure described in Example 27 to give the title compound as a white solid.

Example 59

S-amino-N-[1,1-dimethyl-2-[[1-oxo-3-phenyl-2S-[[[(phenylsulfonyl)amino]carbonyl]amino]propyl]amino]ethyl]-4-hydroxy-2,6-dimethylbenzenepropanamide, monohydrochloride

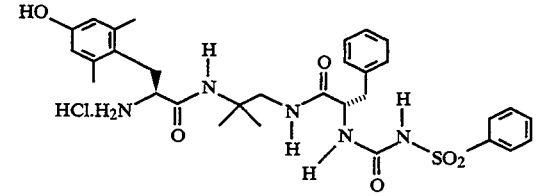

The title compound of Example 58 was treated with HCl by the procedure described in Example 3 to give the title compound as a white solid.

H¹NMR (CD$_3$OD) d: 0.9 (s, 3H), 1.2 (s, 3H), 2.3 (s, 6H). Calculated for C$_{31}$H$_{39}$N$_5$O$_6$S+1.1 HCl+1.25 H$_2$O: C, 55.38; H, 6.37; N, 10.42; Cl, 5.80. Found: C, 55.45; H, 6.23; N, 9.88; Cl, 5.81. $[\alpha]_D = +45.5°$, MeOH.

Example 60

Writhing Assay

The "Writhing Assay" is one of the most widely-used experimental procedures for measuring the analgesic activity of different narcotic and nonnarcotic analgesic agents, and involves the continuous, chemically-induced pain of visceral origin to an animal, such as a mouse or rat. [Gyires et al., *Arch. int. Pharmacodyn*, 267, 131–140 (1984); C. Vander Wende et al., *Fed. Proc.*, 15, 494 (1956); Koster et al., *Fed. Proc.*, 18, 412 (1959); and Witken et al., *J. Pharmacol. Exp. Ther.*, 133, 400–408 (1961).] Chemicals which may be used to induce this pain include phenylbenzoquinone (PBQ) and acetic acid. As a result of the chemical irritation to the animal, a characteristic stretching and writhing of the animal (dorsiflexion of the animal's back, extension of its hindlimbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds within the present invention exhibit analgesic activity in mice, as shown by the results of the Writhing Assay presented in Table I below.

This assay was conducted generally in the manner described by R. I. Taber, "Predictive Value of Analgesic Assays in Mice and Rats," *Advances in Biochemical Psychopharmacology*, 8, 191 (1974).

Two hundred CD Charles River mice, weighing 20 to 30 grams, were used in this assay.

Twenty-five minutes after subcutaneous administration, and fifteen minutes after oral administration, to the mice of 10 mg per kilogram (mpk) of body weight of either a tyrosyl diamide compound of the invention (hereinafter "test compound"), or of the Jacobson Compound, 0.1 mL per 10 g of body weight of a 0.025% w/v solution of phenylbenzoquinone (PBQ) was injected intraperitoneally into each mouse. Some mice were given saline in place of a test compound, or of the Jacobson Compound, and were used as a control group.

Five minutes later, each mouse was individually placed into a glass beaker for observation, and the number of writhes occurring during the following ten-minute period was counted.

A compound was considered to be "active" (to have produced analgesia in a mouse) if, after the administration of 10 mg per kilogram (mpk) of body weight of the compound to the mouse, the number of writhes elicited by a mouse injected with PBQ was equal to, or less than, one-half the median number of writhes recorded for the saline-treated control group of mice that day, as described by R. I. Taber, supra.

The standard initial screening dose of a test compound employed in this assay was 10 mpk per gram of body weight for both routes of administration. If this initial screening dose of the compound produced analgesia in seven of ten mice, then the effect of additional doses of the compound on the writhing response was evaluated, and then the $ED_{50}$ value (that dose of a compound which produced analgesia in 50% of the mice to which the compound was administered) was calculated. A maximum likelihood function was used to determine the $ED_{50}$ value. (The slopes of the dose-response curves for the compounds analyzed were compared as described by Tallarida and Murray, *Manual of Pharmacologic Calculations*, Page 11 (Springer Verlag, N.Y., 1981)).

The results for the compounds analyzed in this assay, and discussed in the examples which correspond thereto, are presented in Table I below, and are expressed in terms of the $ED_{50}$ value. All of the compounds of the present invention tested in this assay were found to be active in all ten of the mice to which the compound was administered when administered subcutaneously at a dose of 10 mpk.

As Table I shows, the tyrosyl diamide compound of the invention shown and synthesized in Example 47 was determined to be the most potent compound of the invention tested in the Writhing Assay, and is the most preferred compound of the invention. As Table I also shows, the compound of the invention shown and synthesized in Example 47 was surprisingly and unexpectedly found to be eight times more potent than the Jacobson Compound when administered to the mice subcutaneously, and seven times more potent than the Jacobson Compound when administered to the mice orally.

TABLE I

| Data Generated from the Writhing Assay | | |
|---|---|---|
| Compound Tested | Subcutaneous (S.C.) $ED_{50}$ | Oral (p.o.) $ED_{50}$ |
| Example No. 47 | 0.2 | 0.6 |
| Example No. 10 | 5 | NT |
| Example No. 16 | 5 | NT |
| Example No. 37 | 5 | NT |
| Example No. 52 | 5 | NT |
| Example No. 18 | 5 | NT |
| Jacobson Compound | 1.6 | 4.1 |

NT = Not Tested

Example 61

Tail Flick and Hot Plate Assays

The "Tail Flick Assay" and the "Hot Plate Assay" (also known as the "Hind Paw Lick Assay") use thermal pain of transient duration, and are tests in which the pain threshold of the mice or rats being analyzed has not been altered. They are useful for evaluating the ability of a compound or drug to increase the animal's pain threshold (i.e. prolong response latencies), rather than to restore normal thresholds.

The heat-induced response to the Tail Flick Assay is a reflex reaction mediated at the level of the spinal cord. The heat-induced response to the Hot Plate Assay, however, is a more complex behavior requiring integration at higher centers in the brain.

When used together, the Tail Flick Assay and Hot Plate Assay provide two different methods of concurrently measuring analgesia in an animal. Compounds which are active in one of the assays may not be active in the other assay.

Opiate compounds having clinical efficacy as analgesics generally increase tail flick and/or hot plate latencies. Thus, morphine and codeine are generally determined to be active in both of these tests. In contrast, aspirin and Zomax, which are Non-Steroidal Antiinflammatory Drugs (NSAIDs), show little activity in either of these tests. However, these tests are not sufficiently sensitive, or of the appropriate design, to demonstrate the analgesic activity of NSAIDs.

The Tail Flick Assay and the Hot Plate Assay were performed generally in the manner described by G. Woolfe et al., "The Evaluation of the Analgesic Action of Pethidine Hydrochloride (Demerol)," *J. Pharmacol. Exp. Ther.*, 80, 300, (1944), F. D'Amour et al., "A Method for Determining Loss of Pain Sensation," *J. Pharmacol. Exp. Ther.*, 72, 74, 300–307 (1941), and E. Drower et al., "The Antinociceptive Effects of Prostaglandin Antagonists in the Rat," *European Journal of Pharmacology*, 133, 249–256 (1987).

Male Charles River albino mice weighing 20 to 30 g were employed in these assays.

Tail flick response latencies (defined as the time that elapsed between the onset of a high intensity beam of light and the reflex removal of the mouse's tail) and hot plate response latencies (defined as the time that elapsed between the placement of a mouse on a 55 degrees Celsius surface and a lick of the hind paw) were separately, but consecutively, measured before (baseline) and again at fixed intervals after subcutaneous administration of the Test Tyrosyl Diamide Compound, or after the administration of saline (controls). The cut-off latencies established to prevent tissue damage in the mice are 12 seconds in the Tail Flick Assay, and 40 seconds in the Hot Plate Assay. The significance of any increase in tail flick response latency or hot plate response latency is determined using analyses of variance.

One way analyses of variance were used to determine the significance of the effect of the Test Tyrosyl Diamide Compound on response latencies. For these assays, the $ED_{50}$ value was defined as the dose of the compound which produced one half the maximum possible increase in latency (i.e., to 7.5 seconds in the Tail Flick Assay, and to 25 seconds in the Hot Plate Assay). Calculations of $ED_{50}$ values were based upon a least squared linear regression equation computed for the data at a time of peak effect, as described by D'Amour and Woolfe, supra.

"Activity" or "Inactivity" was determined at a particular concentration of the compound by a significant increase in tail flick or hot plate latencies above normal latencies.

The data resulting from the Tail Flick Assay and the Hot Plate Assay for the only compound tested in these assays, the compound shown and described in Example No. 47, are presented in Tables II and III below, respectively. The numbers in the tables are calculated $ED_{50}$ values.

TABLE II

| Data Generated from the Tail Flick Assay | |
|---|---|
| Compound Tested | Subcutaneous |
| Example No. 47 | 1.9 |

TABLE III

| Data Generated from the Hot Plate Assay | |
|---|---|
| Compound Tested | Subcutaneous |
| Example No. 47 | 2.4 |

Example 62

Opiate Binding Assay

The Jacobson Compound and compounds within the present invention were also evaluated in an opioid radioligand binding assay, which measures the affinity of opioids for specific opioid receptors in rat forebrain, by their ability to displace the binding of radiolabeled ligands specifically bound to $\mu$ and/or $\delta$ opioid receptors isolated from rat brain. Compounds which are determined to be active in this in vitro assay will generally have opioid-like effects in animals, including analgesia, unless they are not bioavailable.

A purified homogenate of receptor membranes was prepared from the brains of the rats according to the method described by K. J. Chang et al., "Multiple Opiate Receptors: Enkephalins and Morphine Bind to Receptors of Different Specitivity," *J. Biol Chem.*, 254, 2610–2618 (1979).

Male Charles River Sprague-Dawley albino rats weighing 150 to 300 g were stunned and decapitated. Their forebrains (minus the cerebellum and associated hindbrain) were quickly removed and rinsed in ice-cold 50 mM Tris buffer, pH 7.4, and homogenized in 20 volumes of buffer with a Polytron (Brinkman) at setting 6 for 30 seconds. The membranes were washed by centrifugation for 20 minutes at 30,000×g, followed by resuspension to twice the original volume. The homogenate was incubated at 25° for 1 hour, followed by centrifugation as above.

The resulting homogenate was then assayed for protein content according to the method described by Itzhaki et al., "A Micro-Biuret Method for Estimating Proteins," *Anal. Biochem.*, 9, 401–410 (1964). The final pellet was resuspended to a protein concentration of 10 mg protein per mL (assuming 6% of wet weight is protein) and 4 mL aliquots were rapidly frozen in liquid $N_2$.

The binding of compounds to the rat brain opiate receptor membrane preparation containing either $\delta$ or $\mu$ opioid receptors was measured using a modification of the method of C. B. Pert et al., "Properties of Opiate-Receptor Binding in Rat Brain," *Proc. Natl Acad Sci.*, 70, 2243–2247 (1972).

The opiate binding assays were conducted in triplicate at 37° C. in 50 mM Tris/HCl buffer at pH 7.4 in a final volume of 1 mL, using varying concentrations of the compound being evaluated. Each of three tubes contained 0.8 mL of homogenate containing approximately 1 mg/mL of protein. $^3$[H]-DAMPGO (2.0 nM) and $^3$[H]-DSLET (1.0 nM) were used to label the $\mu$ and $\delta$ opiate rat brain receptors, respectively.

The "percent displacement" of radiolabeled ligand ($^3$[H]-DAMPGO for the $\mu$ receptors and $^3$[H]-DSLET for the $\delta$ receptors) bound to the $\mu$ or $\delta$ opioid receptors by a compound was determined at different concentrations of the compound (10 $\mu$M, 1 $\mu$M, 100 nM and/or 1 nM). Because the radiolabeled ligand and the compound compete with each other for the opiate receptor binding sites, the greater the percent of displacement of the bound radiolabeled ligand, the better the compound is in terms of its ability to bind to the opiate receptors and, thus, the more potent is the compound. "Specific binding" of a compound of the present invention to the $\mu$ or the $\delta$ opiate rat brain receptors was defined as the difference between total binding and that in the presence of 10 $\mu$M of levorphanol.

For those compounds which bound particularly well to the opiate receptors, the mean $IC_{50}$ value (that concentration of a particular compound which is required to have 50 per cent of the bound radiolabeled ligand displaced from the opiate receptors) was calculated (nM). $IC_{50}$ values were determined from log-logit plots of concentration vs. time response curves. Comparison of $IC_{50}$ values in this assay system provides a measure of the receptor selectivity of the tested compounds.

Finally, for those compounds for which a mean $IC_{50}$ value was calculated for both the $\mu$ and $\delta$ opioid receptors, the ratio of the mean $IC_{50}$ values for the $\mu$ and $\delta$ opioid receptors was determined. This ratio indicates how selective a particular compound is for the $\delta$ opioid receptors. Thus, if the ratio of the mean $IC_{50}$ values is 1.0, the compound is approximately equally selective for both the μ and the δ opioid receptors. The greater the number is above 1.0, the more specific the compound is for the δ opioid receptors. The smaller the number is below 1.0, the more specific the compound is for the μ opioid receptors.

The results obtained from this opiate binding assay are shown in Table IV below, and correspond to the compound shown and described in the particular example identified below which corresponds thereto. As Table IV shows, compounds within the invention have a good affinity for both the μ and the δ opioid receptors and, thus, would be predicted on this basis to have analgesic activity.

TABLE IV

Data Obtained from the Opiate Binding Assay

| Example Number | Mean IC$_{50}$ Value | Mean IC$_{50}$ μ/δ Ratio |
|---|---|---|
| Jacobson Compound (μ) | 0.6 | 0.3 |
| Jacobson Compound (δ) | 2.0 | 0.3 |
| Example 47 (μ) | 0.4 | 1.3 |
| Example 47 (δ) | 0.3 | 1.3 |
| Example 51 (μ) | NC | NC |
| Example 51 (δ) | >50 | NC |
| Example 52 (μ) | 0.6 | 0.2 |
| Example 52 (δ) | 32 | 0.02 |
| Example 48 (μ) | 0.3 | 0.1 |
| Example 48 (δ) | 2.9 | 0.1 |
| Example 22 (μ) | 2.6 | 0.8 |
| Example 22 (δ) | 3.1 | 0.8 |
| Example 10 (μ) | 3.3 | 0.8 |
| Example 10 (δ) | 4.0 | 0.8 |
| Example 23 (μ) | 1000 | 10 |
| Example 23 (δ) | 100 | 10 |
| Example 11 (μ) | 1000 | 10 |
| Example 11 (δ) | 100 | 10 |
| Example 12 (μ) | 3.4 | 0.1 |
| Example 12 (δ) | 31.4 | 0.1 |
| Example 54 (μ) | 3.3 | 0.04 |
| Example 54 (δ) | 88.8 | 0.04 |
| Example 24 (μ) | 3.7 | 0.01 |
| Example 24 (δ) | 562.2 | 0.01 |
| Example 4 (μ) | 1000 | 10 |
| Example 4 (δ) | 100 | 10 |
| Example 16 (μ) | 0.51 | 0.7 |
| Example 16 (δ) | 0.78 | 0.7 |
| Example 14 (μ) | 0.54 | 0.8 |
| Example 14 (δ) | 0.64 | 0.8 |
| Example 57 (μ) | NC | NC |
| Example 57 (δ) | 100 | NC |
| Example 18 (μ) | 0.33 | 0.07 |
| Example 18 (δ) | 4.7 | 0.07 |
| Example 20 (μ) | 1.2 | 0.06 |
| Example 20 (δ) | 19.3 | 0.06 |
| Example 26 (μ) | 19 | 0.6 |
| Example 26 (δ) | 29.8 | 0.6 |
| Example 8 (μ) | <10 | NC |
| Example 8 (δ) | 28 | NC |
| Example 33 (μ) | <10 | NC |
| Example 33 (δ) | ~2 | NC |
| Example 30 (μ) | <10 | NC |
| Example 30 (δ) | 100 | NC |
| Example 35 (μ) | <10 | NC |
| Example 35 (δ) | ~2 | NC |
| Example 31 (μ) | 100 | NC |
| Example 31 (δ) | >100 | NC |
| Example 28 (μ) | <10 | NC |
| Example 28 (δ) | ~2 | NC |
| Example 37 (μ) | <10 | NC |
| Example 37 (δ) | ~2 | NC |
| Example 39 (μ) | 4.7 | 0.6 |
| Example 39 (δ) | 7.8 | 0.6 |
| Example 41 (μ) | 122 | 0.5 |
| Example 41 (δ) | 257 | 0.5 |
| Example 6 (μ) | 1.1 | 0.6 |
| Example 6 (δ) | 1.8 | 0.6 |
| Example 46 (μ) | 0.88 | 0.2 |
| Example 46 (δ) | 4.2 | 0.2 |
| Example 59 (μ) | 3.2 | 0.4 |
| Example 59 (δ) | 7.3 | 0.4 |

TABLE IV-continued

Data Obtained from the Opiate Binding Assay

| Example Number | Mean IC$_{50}$ Value | Mean IC$_{50}$ μ/δ Ratio |
|---|---|---|
| Example 56 (μ) | 85.5 | 1.7 |
| Example 56 (δ) | 50.3 | 1.7 |

NC = Not Calculated

The foregoing examples are provided to enable one of ordinary skill in the art to practice the present invention. These examples are merely illustrative, however, and should not be read as limiting the scope of the invention as it is claimed in the appended claims.

While the invention has been described and illustrated with reference to certain prepared embodiments thereof, those skilled in the art will appreciate that various changes, modifications and substitutions can be made therein without departing from the spirit and scope of the invention. For example, effective dosages other than the preferred range as set forth hereinabove may be applicable as a consequence of variations in the responsiveness of the animal being treated to induce analgesia, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow, and that such claims be interpreted as broadly as is reasonable.

What is claimed is:

1. A compound having the structure:

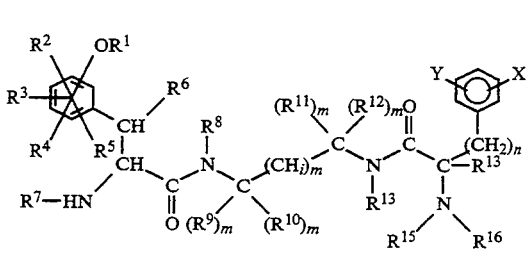

and the pharmaceutically-acceptable salts thereof, wherein:

$R^1$ is hydrogen, alkyl having from 1 to 4 carbon atoms or acetyl;

$R^2$, $R^3$, $R^4$, $R^5$, $R^6$, $R^{14}$, $R^{15}$ and Y may each be the same or different, and are each independently hydrogen or alkyl having from 1 to 4 carbon atoms;

$R^7$ is hydrogen or t-butyloxycarbonyl;

$R^8$ is hydrogen or alkyl having from 1 to 4 carbon atoms, and when alkyl is taken together with $R^9$ or $R^{10}$ when either is alkyl, $-(CH_j)_m-$, $R^{11}$ or $R^{12}$ when either is alkyl and $R^{13}$ when $R^{13}$ is alkyl to form a single-ring, nonaromatic structure;

$R^9$ is hydrogen or alkyl having from 1 to 4 carbon atoms, and when alkyl is taken together with $R^8$ when $R^8$ is alkyl, $-(CH_j)_m-$, $R^{11}$ or $R^{12}$ when either is alkyl and $R^{13}$ when $R^{13}$ is alkyl to form a single-ring, aromatic or nonaromatic structure;

R¹⁰ is hydrogen or alkyl having from 1 to 4 carbon atoms, and when alkyl is taken together with R⁸ when R⁸ is alkyl, —(CH$_i$)$_m$—, R¹¹ or R¹² when either is alkyl and R¹³ when R¹³ is alkyl to form a single-ring, aromatic or nonaromatic structure;

R¹¹ is hydrogen or alkyl having from 1 to 4 carbon atoms, and when alkyl is taken together with R⁸ when R⁸ is alkyl, R⁹ or R¹⁰ when either is alkyl, —(CH$_i$)$_m$—, and R¹³ when R¹³ is alkyl to form a single-ring, aromatic or nonaromatic structure;

R¹² is hydrogen or alkyl having from 1 to 4 carbon atoms, and when alkyl is taken together with R⁸ when R⁸ is alkyl, R⁹ or R¹⁰ when either is alkyl, —(CH$_i$)$_m$—, and R¹³ when R¹³ is alkyl to form a single-ring, aromatic or nonaromatic structure;

R¹³ is hydrogen or alkyl having from 1 to 4 carbon atoms, and when alkyl is taken together with R⁸ when R⁸ is alkyl, R⁹ or R¹⁰ when either is alkyl, —(CH$_i$)$_m$—, and R¹¹ or R¹² when either is alkyl to form a single-ring, nonaromatic structure;

R¹⁶ is hydrogen, acetyl,

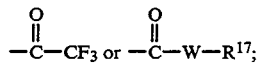

R¹⁷ is alkyl, alkaryl, alkenyl, alkylcarboalkoxy or sulfonylaryl;

X is hydrogen, halogen or alkyl having from 1 to 4 carbon atoms;

W is —CH₂—, oxygen or —NH—;

i is an integer of from 0 to 2; and m is an integer of from 0 to 6, with the proviso that when R¹ is hydrogen or alkyl:
(1) R² and R⁵ are each alkyl having from one to four carbon atoms; and/or
(2) X and Y are each alkyl having from one to four carbon atoms, and with the proviso that R⁸, R⁹, R¹⁰, —(CH$_i$)$_m$—, R¹¹, R¹² and/or R¹³ from a single-ring, aromatic or nonaromatic structure.

2. A compound of claim 1 wherein R¹ is hydrogen or acetyl.

3. A compound of claim 2 wherein R² is hydrogen or methyl.

4. A compound of claim 3 wherein R³ is hydrogen or methyl.

5. A compound of claim 4 wherein R⁴ is hydrogen.

6. A compound of claim 5 wherein R⁵ is hydrogen or methyl.

7. A compound of claim 6 wherein R⁶ is hydrogen.

8. A compound of claim 7 wherein R¹⁴ is hydrogen.

9. A compound of claim 8 wherein R¹⁵ is hydrogen.

10. A compound of claim 9 wherein R¹⁶ is hydrogen or acetyl.

11. A compound of claim 10 wherein Y is hydrogen or methyl.

12. A compound of claim 11 wherein X is hydrogen, methyl or halogen.

13. A compound of claim 12 wherein m is 0, 1 or 2.

14. A compound of claim 13 wherein m is 0 or 1.

15. A compound having pharmaceutical activity, wherein the compound is:

N-[1S-[[4-2S-Amino-3-(4-hydroxy-2,6-dimethylphenyl)-1-oxopropyl]-1-piperazinyl]carbonyl]-2-phenylethyl]acetamide, monohydrochloride;

N-[1-[2S-(Acetylamino)-1-oxo-3-phenylpropyl]-3-pyrrolidinyl]-αS-amino-4-hydroxy-2,6-dimethyl-benzenepropanamide, monohydrochloride; or αS-(Acetylamino)-N-[3[[[2S-amino-3-[4-hydroxy-2,6-dimethylphenyl]-1-oxopropylamino]phenyl]-benzenepropanamide, hydrochloride.

16. A compound having the structure:

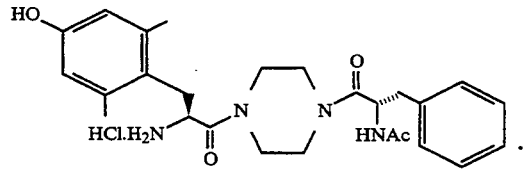

17. A compound having the structure:

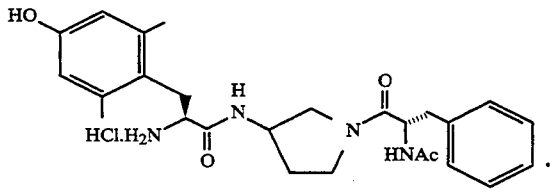

18. A compound having the structure:

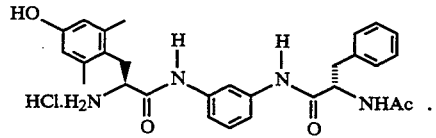

19. A pharmaceutical composition comprising a pharmaceutically-acceptable carrier and a compound of claim 1.

20. A pharmaceutical composition comprising a pharmaceutically-acceptable carrier and a compound having pharmaceutical activity, wherein the compound is:

N-[1S-[[4-[2S-Amino-3-(4-hydroxy-2,6-dimethylphenyl)-1-oxopropyl]-1-piperazinyl]carbonyl]-2-phenylethyl]acetamide, monohydrochloride;

N-[1-[2S-(Acetylamino)-1-oxo-3-phenylpropyl]-3-pyrrolidinyl]-αS-amino-4-hydroxy-2,6-dimethyl-benzenepropanamide, monohydrochloride; or αS-(Acetylamino)-N-[3[[[2S-amino-3-[4-hydroxy-2,6-dimethylphenyl]-1-oxopropylamino]phenyl]-benzenepropanamide, hydrochloride.

21. A method for treating pain in an animal comprising administering to said animal a therapeutically-effective amount of a compound of claim 1.

22. A method for treating pain in an animal comprising administering to said animal a therapeutically-effective amount of a compound having pharmaceutical activity, wherein the compound is:

N-[1S-[[4-[2S-Amino-3-(4-hydroxy-2,6-dimethylphenyl)-1-oxopropyl]-1-piperazinyl]carbonyl]-2-phenylethyl]acetamide, monohydrochloride;

N-[1-[2S-(Acetylamino)-1-oxo-3-phenylpropyl]-3-pyrrolidinyl]-αS-amino-4-hydroxy-2,6-dimethyl-benzenepropanamide, monohydrochloride; or αS-(Acetylamino)-N-[3[[[2S-amino-3-[4-hydroxy-2,6-dimethylphenyl]-1-oxopropylamino]phenyl]-benzenepropanamide, hydrochloride.

* * * * *

UNITED STATES PATENT AND TRADEMARK OFFICE
CERTIFICATE OF CORRECTION

PATENT NO. : 5,364,850           Page 1 of 3
DATED       : November 15, 1994
INVENTOR(S) : Hansen, Jr., et al.

It is certified that error appears in the above-indentified patent and that said Letters Patent is hereby corrected as shown below:

In the abstract, and in column 3, line 50, that part of the structure reading

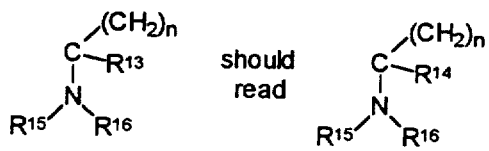

Column 2, line 50, reading "short-Chain" should read -- short-chain --.

Column 3, line 36, reading "J Med Chem.," should read -- J. Med. Chem., --.

Column 12, line 40, reading "et al.." should read -- et al., --.

Column 17, line 45, that part of the structure reading

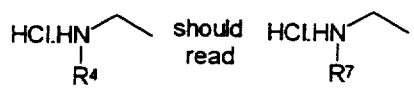

Column 19, line 61, reading "When $R^{16}=$" should read -- c) When $R^{16}=$ --.

Column 28, line 13, reading "Phenylmethyl]" should read -- Phenylmethyl[ --.

Column 28, line 43, reading "dimethylphenyl-phenyl)" should read -- dimethylphenyl) --.

UNITED STATES PATENT AND TRADEMARK OFFICE
CERTIFICATE OF CORRECTION

PATENT NO. : 5,364,850      Page 2 of 3
DATED      : November 15, 1994
INVENTOR(S): Hansen, Jr., et al.

It is certified that error appears in the above-indentified patent and that said Letters Patent is hereby corrected as shown below:

Column 29, line 64, reading "$H_2O - 1$ HCl" should read -- $H_2O + 1$ HCl --.

Column 30, line 27, reading "dimethylphenyl-1-" should read -- dimethylphenyl)-1- --.

Column 31, line 13, reading "0,494 g" should read -- 0.494 g --.

Column 37, line 35, reading "+38.4°," should read -- +28.4°, --.

Column 47, line 31, reading "109.0" should read -- 109.9 --.

Column 48, line 21, reading "(s, 3H), (s, 3H)," should read -- (s, 3H), 2.27 (s, 3H), Column 56, line 2, reading "J. Biol Chem.," should read -- J. Biol. Chem., --.

Column 56, line 28, reading "Natl Acad Sci.," should read -- Natl. Acad. Sci., --.

Column 58, line 43, that part of the structure reading

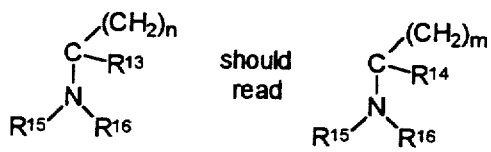

UNITED STATES PATENT AND TRADEMARK OFFICE
CERTIFICATE OF CORRECTION

PATENT NO. : 5,364,850
DATED : November 15, 1994
INVENTOR(S) : Hansen, Jr., et al.

It is certified that error appears in the above-indentified patent and that said Letters Patent is hereby corrected as shown below:

Column 59, line 65, reading "[[4-2S" should read -- [[4-[2S --.

Column 60, line 30, that part of the structure reading

Signed and Sealed this

Second Day of January, 1996

Attest:

BRUCE LEHMAN

Attesting Officer        Commissioner of Patents and Trademarks